United States Patent
Alper

(10) Patent No.: US 9,840,560 B2
(45) Date of Patent: Dec. 12, 2017

(54) MONOCLONAL ANTIBODIES TO EGFR, AND USES THEREFOR

(71) Applicant: Alper Biotech LLC, Rockville, MD (US)

(72) Inventor: Özge Alper, North Bethesda, MD (US)

(73) Assignee: ALPER BIOTECH LLC, Rockville, MD (US)

( * ) Notice: Subject to any disclaimer, the term of this patent is extended or adjusted under 35 U.S.C. 154(b) by 0 days.

(21) Appl. No.: 14/209,976

(22) Filed: Mar. 13, 2014

(65) Prior Publication Data
US 2014/0271477 A1    Sep. 18, 2014

Related U.S. Application Data

(60) Provisional application No. 61/790,698, filed on Mar. 15, 2013.

(51) Int. Cl.
*A61K 39/395*    (2006.01)
*C07K 16/28*    (2006.01)
*G01N 33/566*    (2006.01)

(52) U.S. Cl.
CPC ....... *C07K 16/2863* (2013.01); *G01N 33/566* (2013.01); *G01N 2333/485* (2013.01)

(58) Field of Classification Search
None
See application file for complete search history.

(56) References Cited

U.S. PATENT DOCUMENTS

2006/0210564 A1* 9/2006 Kumagai ........... C07K 16/2809
                                                                424/145.1

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*
Skolnick and Fetrow. From genes to protein structure and function: novel applications of computational approaches in the genomic era. Trends in Biotechnology, 2000. vol. 18, pp. 34-39.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Bendig (1995) Methods: a companion. Methods in Enzymology *: 83-93.*
Paul (1993) Fundamental Immunology, #rd edition, pp. 292-295.*
MacCallum et al. (1996) J. Mol. Biol. 262: 732-745.*

* cited by examiner

*Primary Examiner* — Michael Pak
(74) *Attorney, Agent, or Firm* — Kenealy Vaidya LLP

(57) ABSTRACT

The present invention relates to isolated monoclonal anti-EGFR antibodies, and to the use of such antibodies and antibody fragments to detect EGFR, particularly those expressed by cancer cells. The antibodies are useful in diagnostic as well as therapeutic indications. Methods, devices and kits for the immunodetection and immunotherapy of cells expressing EGFR is also encompassed.

12 Claims, 26 Drawing Sheets

| Light Chain (VL) | MTQSPSSLSASLGERVSLTCQASQGISNNLNWYQQTPGKAPRLLIYDASKLEDGVPSRFSGTGYRTDFNFTISSLEEDVATYFCLQHRYLPVHVRRGDQVGNKTG (SEQ ID NO:1) |
|---|---|
| Heavy Chain (VH) | LVTLKVCGPGILQPSQTLSLTCSFSGFSLSTSGMGVGWLRQPSGKSLEWLAHIWWDDDKRYNPALKSRLTISKDTSSNQVFLKIASVDTTDTATYYCARMGMTGYFDFWGQGTTLTVSS (SEQ ID NO:2) |

FIG. 1A

Light Chain CDRs
- CDR1: QGISNN (SEQ ID NO:3)
- CDR2: DAS (SEQ ID NO:4)
- CDR3: LQHRYLPVH (SEQ ID NO:5)

Heavy Chain CDRs
- CDR1: GFSLSTSGMG (SEQ ID NO:6)
- CDR2: IWWDDDK (SEQ ID NO:7)
- CDR3: ARMGMTGYFDF (SEQ ID NO:8)

```
                                                              CDR3 - IMGT
091215-03_E24_5-T3.ab1       cag cat agg tat ctc ccc gta cac gtt cgg agg ggg gac caa gtt
AJ231256 Musmus IGKV11-125*01 F
V01563 Musmus IGKV14-111*01 F    t   gat g-g t-t ttt cc
AY591690 Musmus IGKV14-126*01 F      g-t c-g agt ttt cc
AJ231243 Musmus IGKV14-100*01 F  t   gct g-g t-t ttt cc
AJ231241 Musmus IGKV14-130*01 F  tt  tat g-g t-t ttt cc
```

FIG. 2H

```
                                                       gga aat aaa acg ggc tga 091215-03_E24_5-T3.ab1
AJ231256 Musmus IGKV11-125*01 F
V01563  Musmus IGKV14-111*01 F
AY591690 Musmus IGKV14-126*01 F
AJ231243 Musmus IGKV14-100*01 F
AJ231241 Musmus IGKV14-130*01 F
```

|  |  |  |  |  |  | 80 |  |  |  |  |  | FR3 - IMGT 85 |  |  |  |  | 90 |  |
|---|---|---|---|---|---|---|---|---|---|---|---|---|---|---|---|---|---|---|
| ctg | aca | atc | tcc | aag | gat | acc | tcc | agc | aac | cag | gta | ttc | ctc | aag |
| --c | --- | --- | --- | --- | --- | --- | --- | -aa | --- | --- | --- | --- | --- | --- |
| --c | --- | --- | --- | --- | --- | --- | --- | -a- | --a | --- | --- | --- | --- | --- |
| --c | --- | --- | --- | --- | --- | --- | --- | -a- | --- | --- | --- | --- | --- | --- |
| --c | --- | --- | --- | --- | --- | --- | --- | -a- | --- | --- | --- | --- | --- | --- |

091215-03_M22_1-T3
AC087166 Musmus IGHV8-8*01 F
AC073939 Musmus IGHV8-11*01 F
AC073939 Musmus IGHV8-12*01 F
AC074329 Musmus IGHV8-5*01 F
U23022 Musmus IGHV8-9*02 [F]

```
                                      CDR3 - IMGT
                                 |----------------------|
                                 cga atg ggc atg acc ggc tac ttt gac ttt tgg ggc caa ggc acc
091215-03_M22_1-T3
AC087166 Musmus IGHV8-8*01 F     --- --- --- --a --- --- --- --- --- --- --- --- --- ---
AC073939 Musmus IGHV8-11*01 F    --- --- --- --a --- --- --- --- --- --- --- --- --- ---
AC073939 Musmus IGHV8-12*01 F    --- --- --- -ga --- --- --- --- --- --- --- --- --- ---
AC074329 Musmus IGHV8-5*01 F     --- --- --- --a --- --- --- --- --- --- --- --- --- ---
023022 Musmus IGHV8-8*02 [F]     -a- --- --- --- --- --- --- --- --- --- --- --- --- ---
```

FIG. 3H

```
091215-03_M22_1-T3         act ctc aca gtc tcc tca g
AC087166 Musmus IGHV8-8*01 F
AC073939 Musmus IGHV8-11*01 F
AC073939 Musmus IGHV8-12*01 F
AC074329 Musmus IGHV8-5*01 F
U23022  Musmus IGHV8-8*02 [F]
```

FIG. 3I

SKBR3 cells

A431 cells

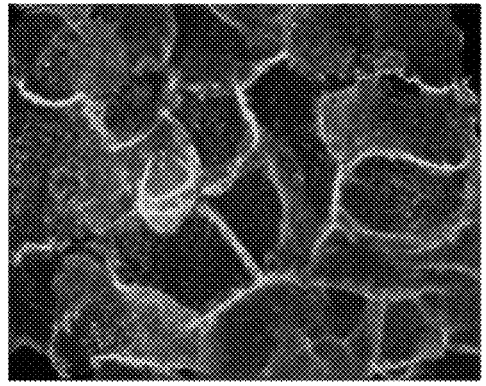
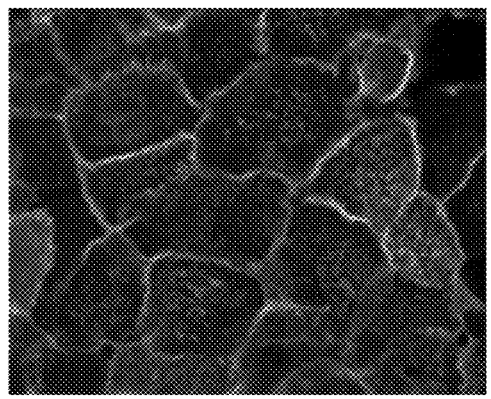
FIG. 6A  Millipore EGFR Moab 05-101
FIG. 6B  Abcam EGFR Moab ab93051
FIG. 6C  Alper Biotech EGFR Moab AB-13

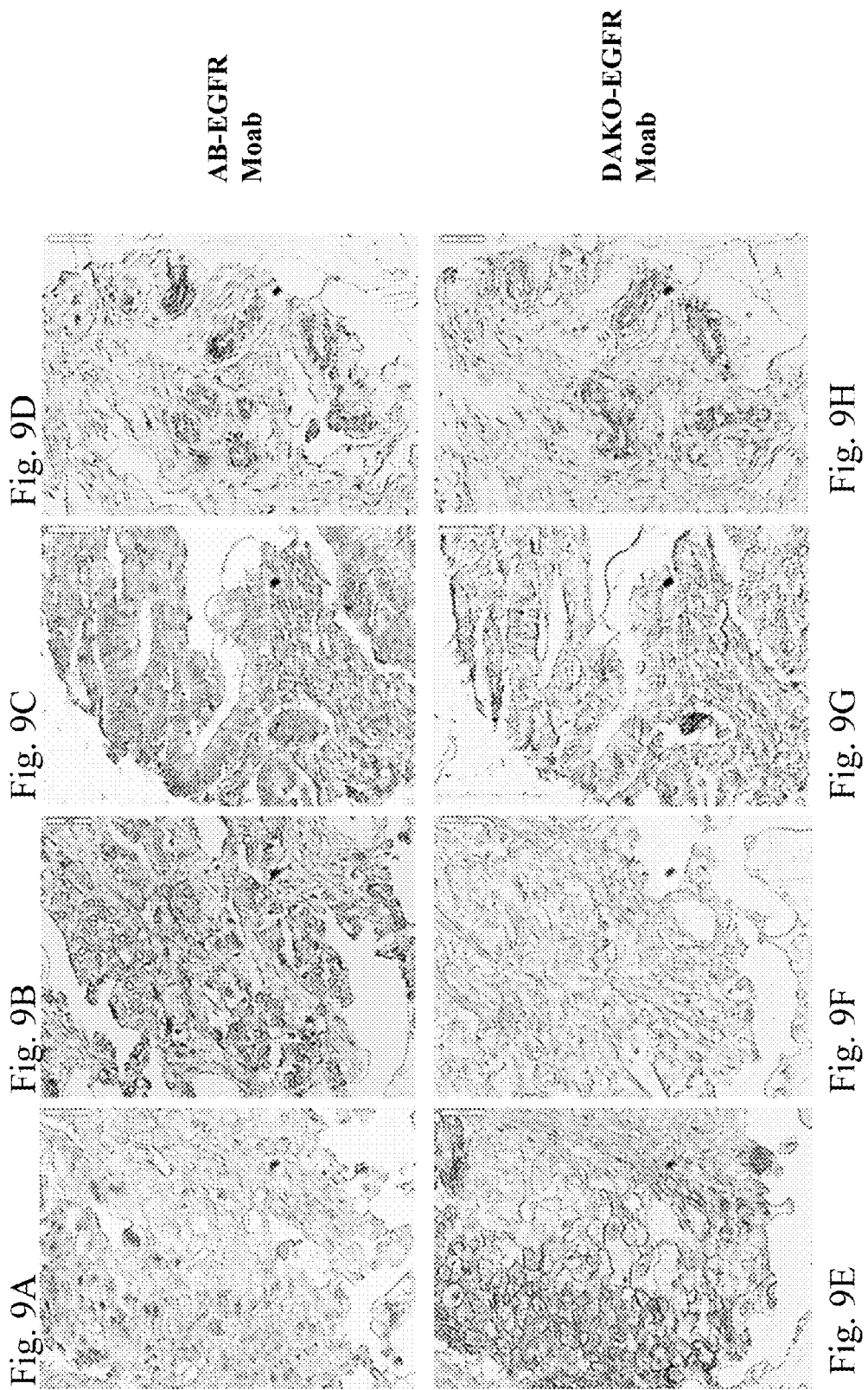

MONOCLONAL ANTIBODIES TO EGFR, AND USES THEREFOR

BACKGROUND & SUMMARY

The present invention relates to antibodies and antibody fragments, and methods of making and using these antibodies and antibody fragments, in the diagnosis, prognosis, prevention and treatment of diseases. The antibodies and antibody fragments are capable of binding to soluble and membrane bound EGFR, as well as to phosphorylated EGFR with high specificity, high sensitivity, and high affinity, and are thus useful in both therapeutic and diagnostic applications.

The epidermal growth factor receptor (EGFR; ErbB; ErbB-1; HER1), a 170 kDa transmembrane glycoprotein encoded by the human HER1 gene, is a member of the protein kinase superfamily. EGFR is a cell-surface receptor that is a member of the epidermal growth factor family (EGF-family). It consists of an extracellular ligand binding domain, a transmembrane domain and an intracellular domain with intrinsic protein-tyrosine kinase activity. See Modjtahedi et al. (1996) Br. J. Cancer 73: 228-235; Herbst and Shin (2002) Cancer 94: 1593-1611. The soluble form of EGFR is secreted from cells and can be recognized using the anti-EGFR antibodies disclosed herein. See Weber and Gill (1984) Science 224: 294-297.

EGFR binds to different ligands, including, but not limited to, epidermal growth factor (EGF), transforming growth factor-alpha (TGF-alpha), amphiregulin, heparin-binding EGF (hb-EGF), betacellulin, and epiregulin. See Herbst and Shin (2002) Cancer 94: 1593-1611; Mendelsohn and Baselga (2000) Oncogene 19: 6550-65.

EGFR has been associated with many pathological disorders. For example, overexpression of EGFR has been reported in numerous human malignant conditions, including cancers of the bladder, brain, head and neck, pancreas, lung, including non-small cell lung cancer, breast, ovary, colon, prostate, and kidney. See Atalay et al. (2003) Ann. Oncology 14: 1346-1363; Herbst and Shin (2002) Cancer 94: 1593-1611; Modjtahedi et al. (1996) Br. J. Cancer 73: 228-235. In many of these conditions, the overexpression of EGFR correlates or is associated with poor prognosis of the patients. Id.

EGFR is abnormally activated (e.g., overexpressed, mutated) in many epithelial tumors, including non-small cell lung cancer, breast cancer, colorectal cancer, head and neck cancers, and prostate cancer. See Adams, G. and Weiner, L. (2005) Nature Biotechnology, 23: 1147-1157. Abnormal activation of EGFR can arise from overexpression of the receptor, gene amplification, activating mutations, overexpression of receptor ligands, and/or loss of regulators of EGFR activity. See Baselga, J. and Arteaga (2005) J. of Clin. Oncol. 23: 2445-2459. Abnormally high EGFR activation results in phosphorylation of several intracellular substrates, which in turns gives rise to mitogenic signaling as well as other tumor-inducing activities. Consequently, EGFR is a target for anti-cancer therapeutic strategies which can potentially inhibit or reduce the receptor's aberrant expression, and/or its activation.

Anti-cancer agents that target EGFR include monoclonal antibodies. The chimeric monoclonal antibody C225 (or cetuximab), which contains the murine variable region of mAb225 and a human IgG1 constant region, is presently available for treatment of certain types of colon cancer in at least the United States and Europe. See Baselga, J. and Arteaga, C. (2005) J. of Clin. Oncol. 23: 2445-2459. The fully human antibody ABX-EGF (panitumumab) is also approved in at least the United States, Europe, and Canada for the treatment of metastatic colorectal cancer. Panitumumab has been reported to have an affinity for EGFR approximately 8-fold greater than that of C225. See Yang, X-D et al. (2001) Crit. Rev. Oncol./Hemat. 38: 17-23. Another humanized anti-EGFR monoclonal antibody, EMD72000 (matuzumab), was in phase II clinical trials in the United States for the treatment of colorectal, lung, esophageal and stomach cancers. See Vanhoefer, U. et al. (2004) J. Clin Oncol. 22: 175-184. It has also been reported that the affinity of humanized antibody h-R3 for EGFR is less than that of C225. See Crombet, T. et al. (2004) J. Clin. Oncol. 22: 1646-1654. Complications, such as skin toxicity that results in flushing, seborrheic dermatitis, and acneform rash have been observed in the clinic with doses of C225 higher than 100 mg/m². See Herbst, R. and Langer, C. (2002) Semin. Oncol. 29: 27-36. Thus, there is a need for anti-EGFR antibodies that are highly sensitive, highly specific and have high affinity to EGFR for therapeutic purposes.

Anti-EGFR antibodies are also used diagnostically. For example, an anti-EGFR antibody contained in the "EGFR pharmDX™" kit from Dako is FDA-approved for identifying patients with colorectal cancer eligible for treatment with cetuximab or panitumumab. However, there is no evidence that the antibody in this kit recognizes soluble EGFR. Thus, the kit is useful in immunohistochemical (IHC) assays, but would not be useful in assays biological fluids such as blood, serum, urine or plasma.

Available diagnostic anti-EGFR antibodies have limited use since they do not recognize soluble EGFR such as would be found in the blood, serum, plasma, or urine. There is a need for anti-EGFR antibodies that are highly sensitive, highly specific and have high affinity to soluble and membrane bound EGFR for diagnostic purposes. There is also a need for anti-EGFR antibodies that are able to recognize the soluble and phosphorylated form of EGFR so that assays can be conducted on blood, plasma, serum, and urine samples rather than tissue biopsies. Less invasive procedures for detecting aberrant EGFR expression, and thus diagnosing EGFR-related diseases and conditions could be accomplished with such an antibody.

The invention is based in part on the creation of an anti-EGFR monoclonal antibody with superior and unexpected beneficial properties, including, but not limited to: a capability to bind to the extracellular domain of EGFR; a capability to bind to the soluble form of EGFR; a capability to bind to a phosphorylated form of the antibody; a superior binding affinity to EGFR; an extra-high selectivity and specificity to EGFR; improved blocking properties; extra-low immunogenicity; extra low toxicity; increased utility for targeting EGFR-expressing cells; increased Fc receptor binding and increased effector function.

Additional objects and advantages of the invention will be set forth in part in the description which follows. The objects and advantages of the present invention will be realized and attained by means of the elements and combinations particularly pointed out in the appended claims.

It is to be understood that both the foregoing general description and the following detailed description are exemplary and explanatory only and are not restrictive of the present invention, as claimed.

BRIEF DESCRIPTION OF THE DRAWINGS

FIGS. 1A and 1B provide the CDR and variable domain sequences of AB-EGFR mAb. Framework regions (FWRs)

of the light chain (VL) and the heavy chain (VH) of AB-EGFR mAb, with the CDRs in bold and underline, are provided in FIG. 1A. The CDRs of the light chain and the heavy chain of AB-EGFR mAb are listed in FIG. 1B.

Figure 2A:
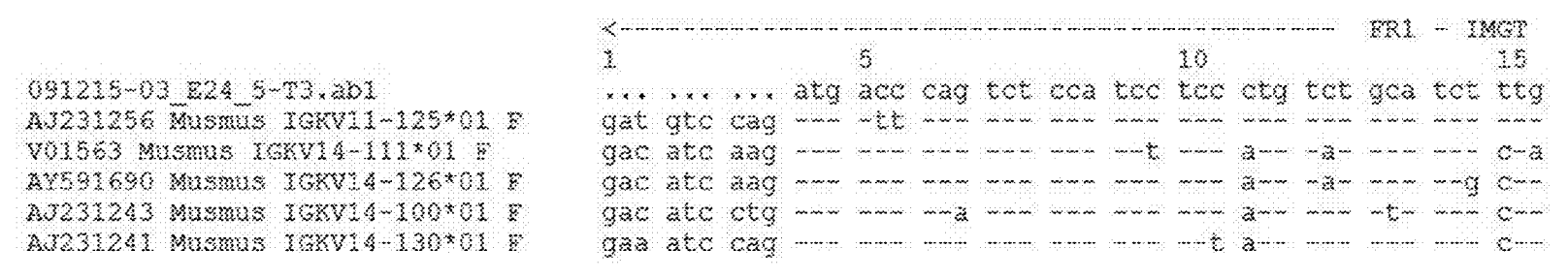
Figure 2B:
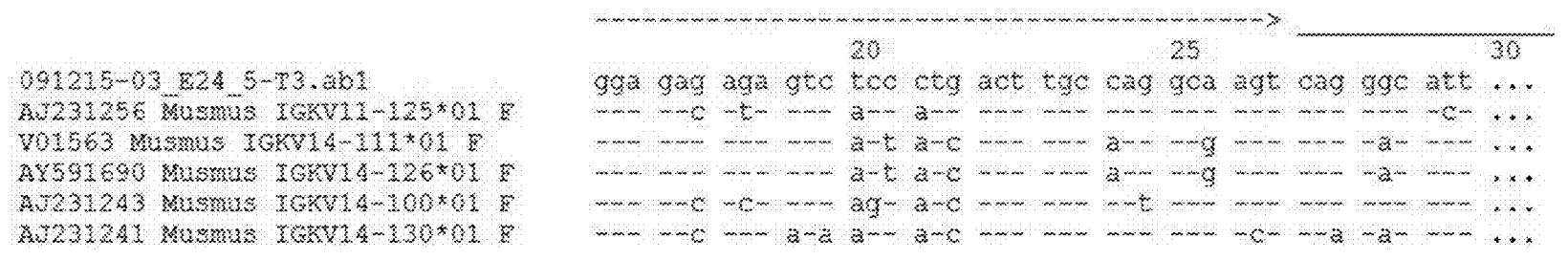
Figure 2C:
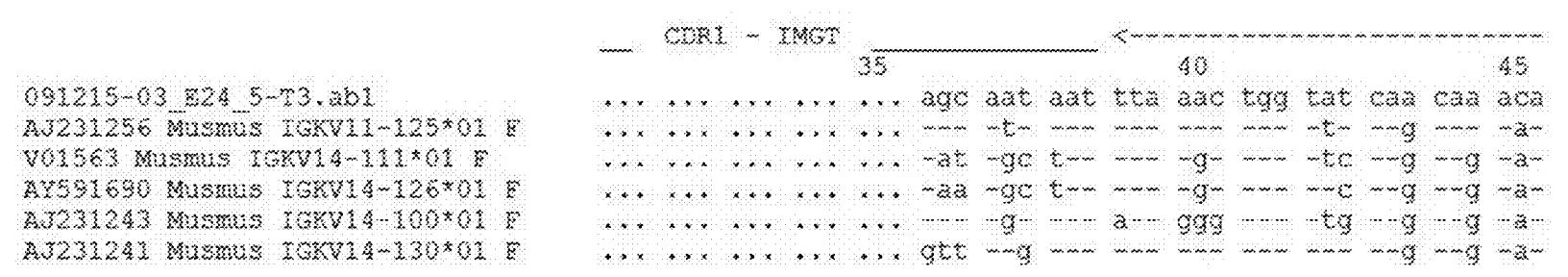
Figure 2D:
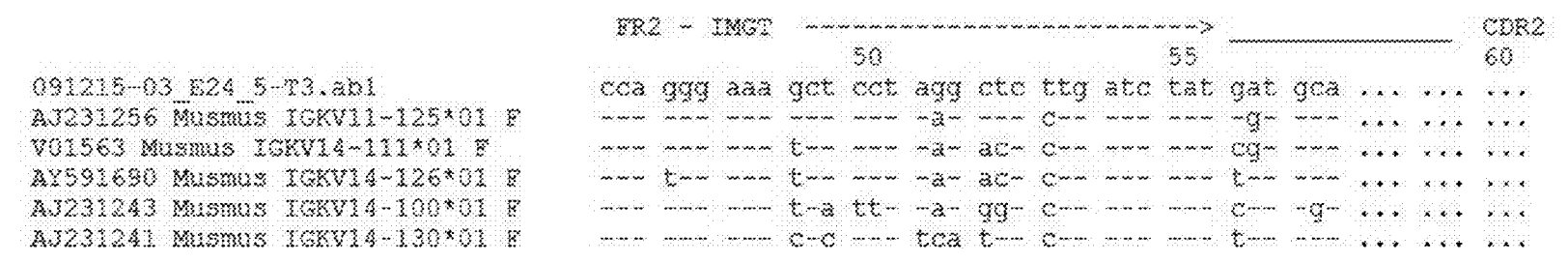
Figure 2E:
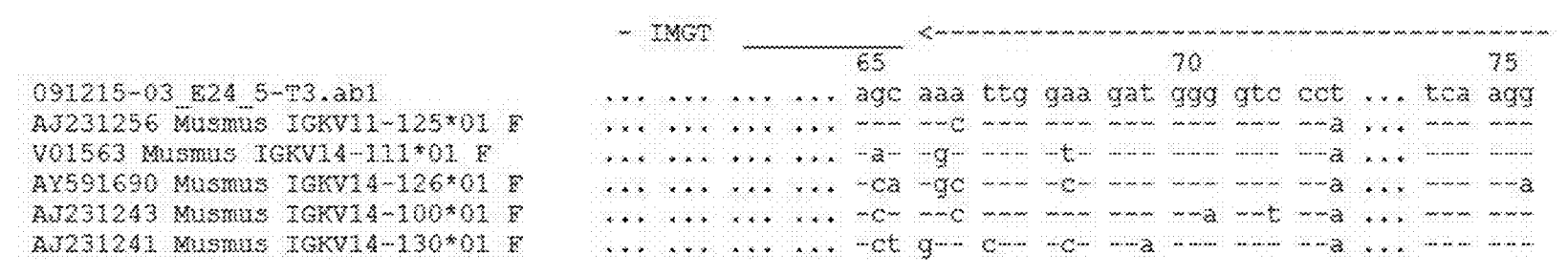
Figure 2F:
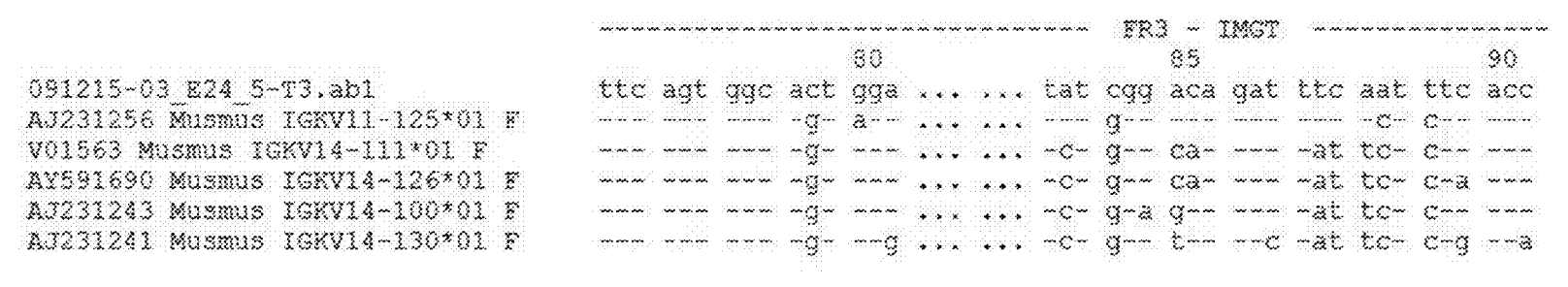

FIGS. 2A, 2B, 2C, 2D, 2E, 2F, 2G, 2H and 2I show the nucleotide sequence of the variable domain of the light chain (VL) of AB-EGFR mAb (top sequence).

Figure 3A:
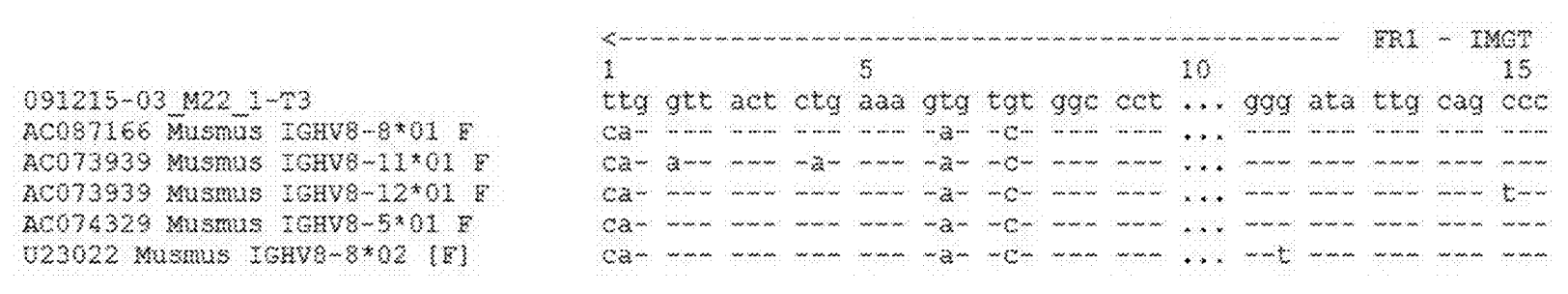
Figure 3B:
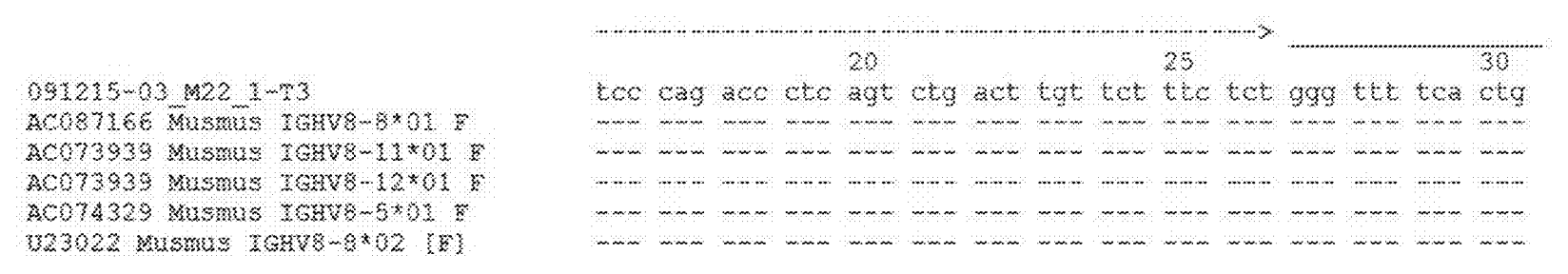
Figure 3C:
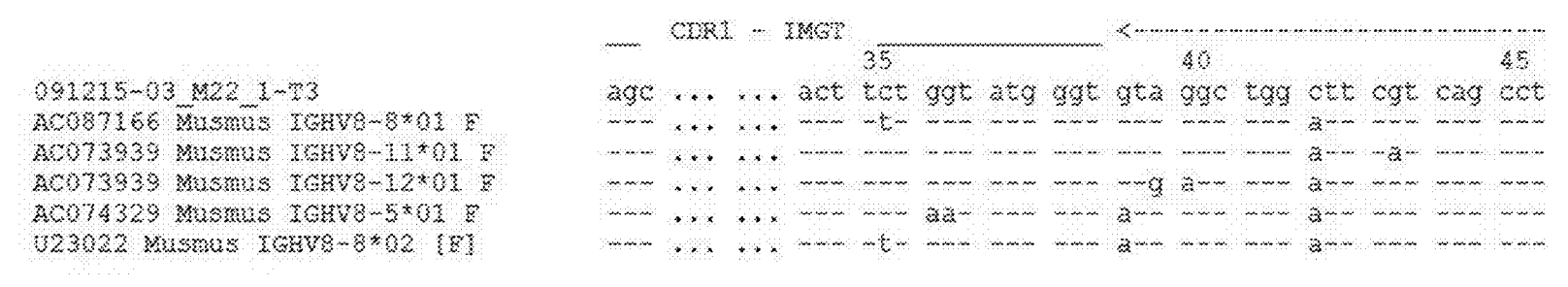
Figure 3D:
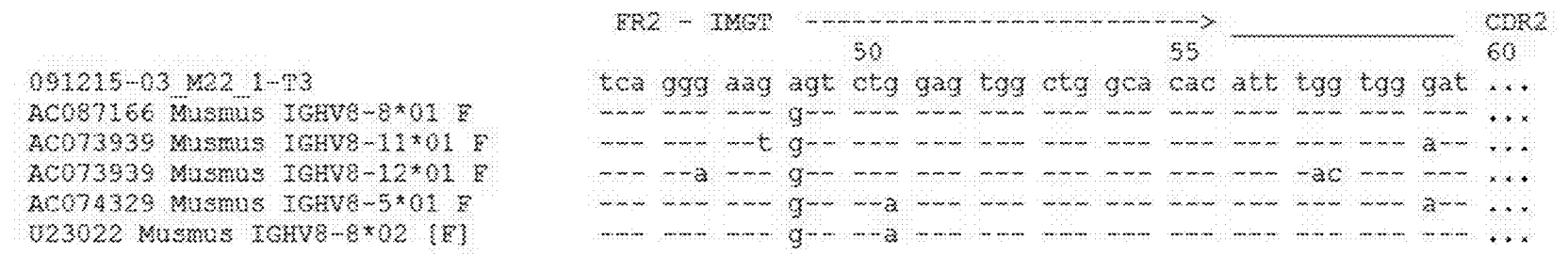
Figure 3E:
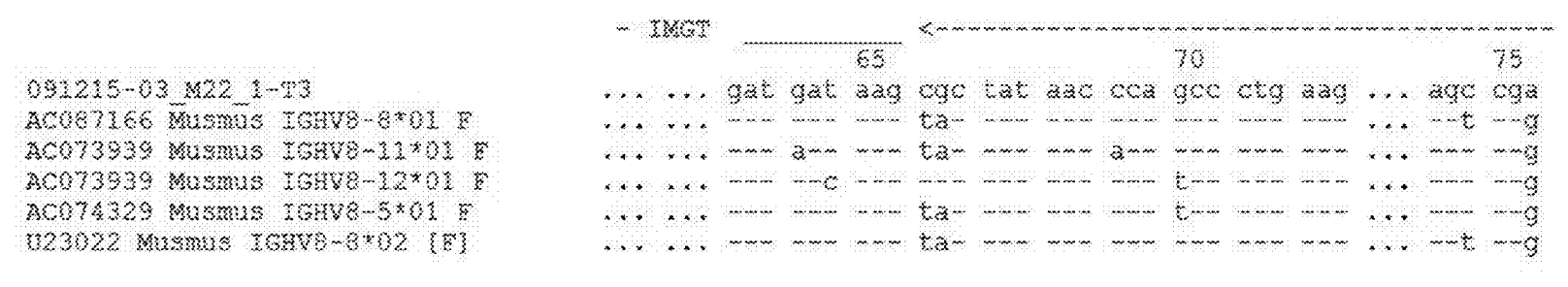

FIGS. 3A, 3B, 3C, 3D, 3E, 3F, 3G, 3H and 3I show the nucleotide sequence of the variable domain of the heavy chain (VH) of AB-EGFR mAb (top sequence).

Figure 4:
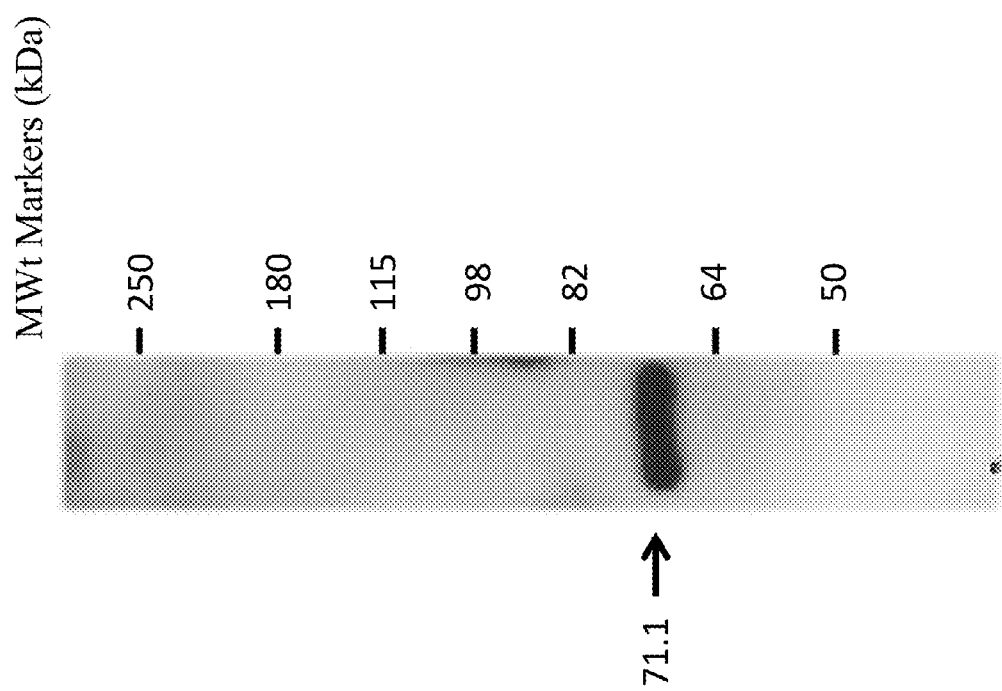

FIG. 4 shows a Western Blot analysis of recombinant EGFR protein immunoblotted with AB-EGFR mAb.

Figure 5B:
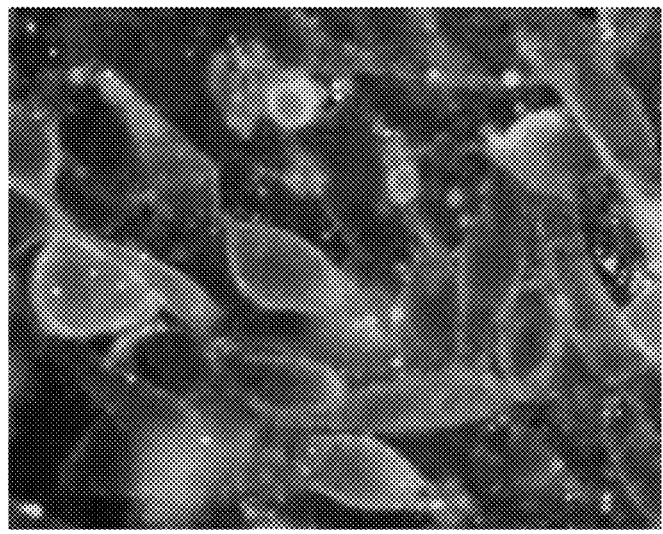
Figure 5A:
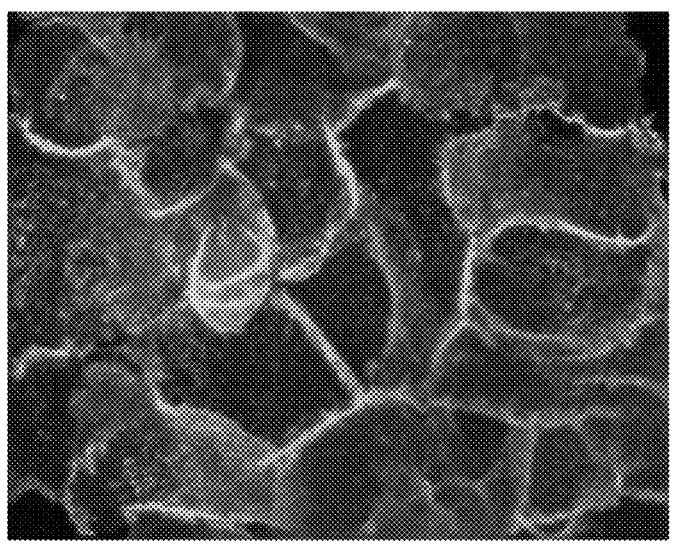

FIGS. 5A and 5B show immunofluorescent staining with AB-EGFR mAb of EGFR-expressing human vulva cancer cell line A-431 cells (FIG. 5A) and human breast cancer cell line SKBR3 cells (FIG. 5B).

FIGS. 6A, 6B and 6C shows immunofluorescent staining of EGFR-expressing human vulva cancer cell line A-431 cells with AB-EGFR mAb and commercially available anti-EGFR antibodies: Millipore monoclonal anti-EGFR antibody 05-101 (FIG. 6A), and Abcam monoclonal anti-EGFR antibody ab93051 (FIG. 6B), and AB-EGFR mAb (FIG. 6C).

Figure 7:
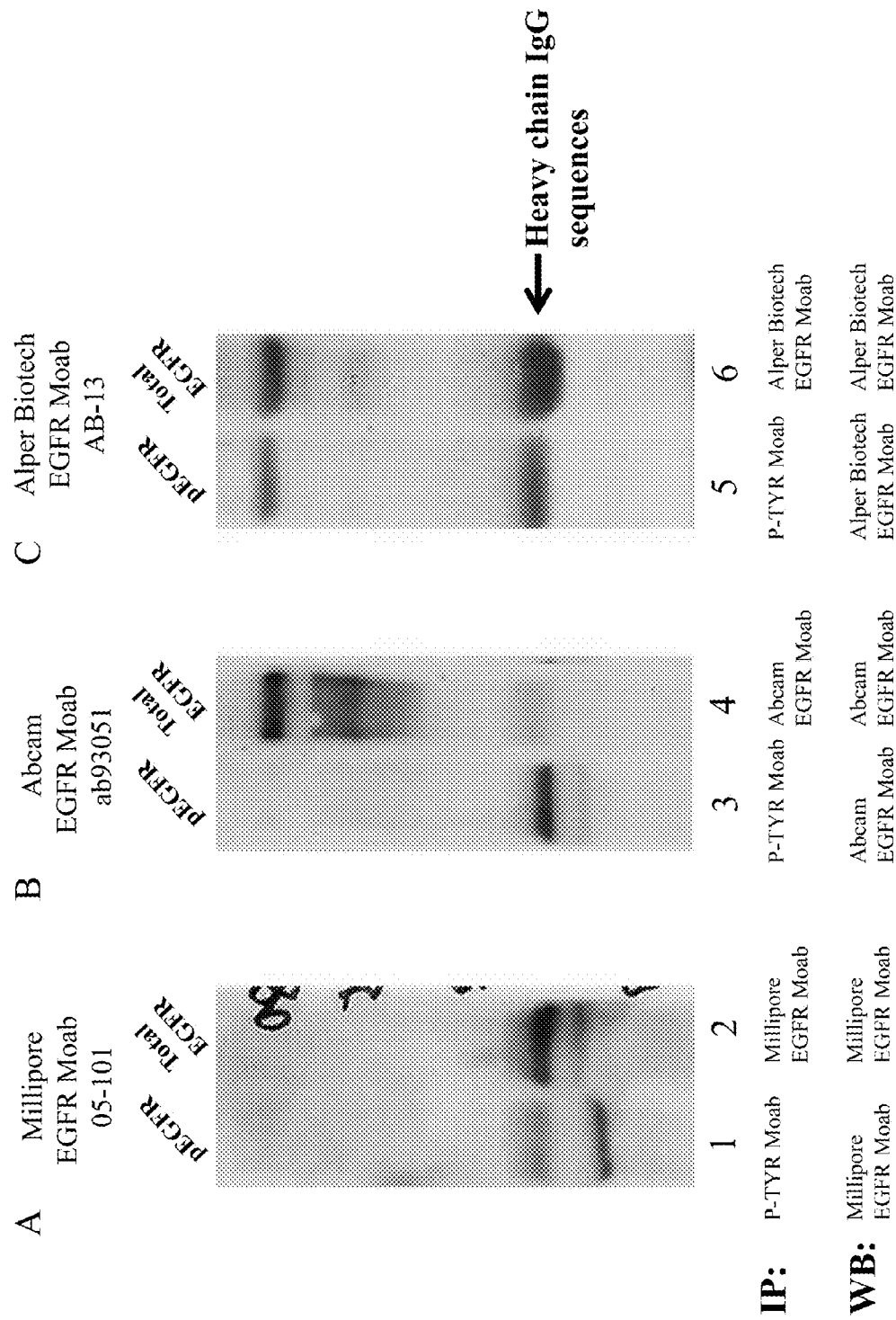

FIG. 7 shows a Western Blot analysis of phosphorylated EGFR (lanes 1, 3, and 5; "pEGFR") and total EGFR (2, 4, and 6) with AB-EGFR mAb and commercially available anti-EGFR antibodies: Millipore monoclonal anti-EGFR antibody 05-101, and Abcam monoclonal anti-EGFR antibody ab93051.

Figure 8B:
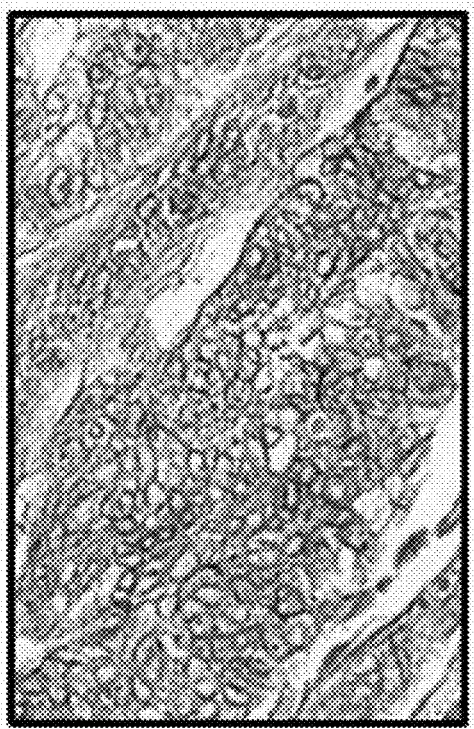
Figure 8A:

FIGS. 8A and 8B show immunohistochemical staining of EGFR expressed in human lung (FIG. 8A) and colon cancer (FIG. 8B) tissues with AB-EGFR mAb.

FIGS. 9A, 9B, 9C, 9D, 9E, 9F, 9G and 9H show immunohistochemical staining of EGFR expressed in human breast cancer tissues with AB-EGFR mAb (top row) and DAKO-EGFR mAb (bottom row).

BRIEF DESCRIPTION OF THE SEQUENCES

SEQ ID NO: 1 shows the amino acid sequences of the variable domain of the light chain of AB-EGFR mAb.

SEQ ID NO: 2 shows the amino acid sequences of the variable domain of the heavy chain of AB-EGFR mAb.

SEQ ID NO: 3 shows the amino acid sequences of CDR1 of the light chain of AB-EGFR mAb.

SEQ ID NO: 4 shows the amino acid sequences of CDR2 of the light chain of AB-EGFR mAb.

SEQ ID NO: 5 shows the amino acid sequences of CDR3 of the light chain of AB-EGFR mAb.

SEQ ID NO: 6 shows the amino acid sequences of CDR1 of the heavy chain of AB-EGFR mAb.

SEQ ID NO: 7 shows the amino acid sequences of CDR2 of the heavy chain of AB-EGFR mAb.

SEQ ID NO: 8 shows the amino acid sequences of CDR3 of the heavy chain of AB-EGFR mAb.

DESCRIPTION OF THE EMBODIMENTS

EGFR has been associated with many cancers, such as cancers of the breast, lung, colon and pancreas. Accordingly, there is a need to develop anti-EGFR antibodies and antibody fragments of high sensitivity, specificity and affinity to diagnose and treat such cancers.

The present invention relates to isolated anti-EGFR monoclonal antibodies and antigen-binding fragments thereof that bind to EGFR with high affinity, sensitivity and specificity. The novel antibodies and antigen-binding antibody fragments are superior to known anti-EGFR antibodies in part because they recognize soluble and phosphorylated forms of EGFR. This renders the antibodies useful in immunoassays of non-tissue biological samples, such as, for example, whole blood, plasma, serum, and urine. The anti-EGFR antibodies are also superior to known anti-EGFR antibodies in immunoassays of tissues and cells since they are highly specific and sensitive. Thus, the isolated antibodies of the present invention may be useful in a variety of immune-detection assays to detect and diagnose EGFR-related diseases, including cancer.

Because the antibodies are so specific and so sensitive, the antibodies and antibody fragments can detect antigen in very small volumes of whole blood, plasma, serum, and urine. For example, the antibodies of the invention can be used to detected antigen in as little as 1 microliter ($\mu$l) of whole blood from patients with or at risk for having an EGFR-related cancer. The antibody is also capable of detecting EGFR-expressing circulating tumor cells in as little as 1 microliter ($\mu$l) of whole blood, plasma, serum, and urine. Thus, the antibodies and antigen-binding fragments of the present invention are useful in in vitro and in vivo assays to detect EGFR and to diagnose EGFR-related diseases.

The present invention also relates to therapeutic uses and methods. The disclosed anti-EGFR monoclonal antibodies and antigen-binding fragments, as well as humanized version of these antibodies, can be administered to patients diagnosed with EGFR-related disorders, as a monotherapy or in combination with other therapies such as chemotherapy and/or radiation therapy.

The disclosed anti-EGFR antibodies and antigen-binding fragments thereof can be used in vivo to deliver or target agents to EGFR-expressing cells or structures. For example, the anti-EGFR antibodies and antibody fragments can be linked, fused, bonded, or associated with therapeutic agents and administered to patients in need.

DEFINITIONS

As used herein, the terms "antibody," "antibodies," and "immunoglobulins" refer to antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')$_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the term "AB-EGFR" describes an antibody comprising at least one of the heavy chain CDRs and at least one light chain CDRs described in FIG. 1B.

The term "isolated antibody" refers to a protein or peptide produced from cDNA-, recombinant RNA-, or any other synthetic-origin, or some combination thereof; as well as to proteins and peptides that, by virtue of their origin or source of derivation, either (1) are not associated with proteins found in nature, (2) are free of other proteins from the same source, e.g. free of murine proteins, (3) are expressed by a cell from a different species, or (4) do not occur in nature.

A "variable domain sequence" refers to an amino acid sequence which can form the structure of an immunoglobulin variable domain. For example, the sequence may include all or part of the amino acid sequence of a naturally-occurring variable domain. For example, the sequence may or may not include one, two or more N- or C-terminal amino acids, or may include other alterations that are compatible with formation of the protein structure.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by hybridoma cells that are uncontaminated by other immunoglobulin producing cells. Alternatively, the monoclonal antibody may be produced by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. The term "monoclonal" is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be made by the hybridoma method first described by Kohler et al., (1975) Nature 256: 495.

The term "chimeric antibodies" includes antibodies in which at least one portion of the heavy and/or light chain is identical with or homologous to corresponding sequences in antibodies derived from a particular species or belonging to a particular antibody class or subclass, and at least one other portion of the chain(s) is identical with or homologous to corresponding sequences in antibodies derived from another species or belonging to another antibody class or subclass, as well as fragments of such antibodies, so long as they exhibit the desired biological activity. See U.S. Pat. No. 4,816,567; Morrison et al., (1984) Proc. Natl. Acad. Sci. USA 81: 6851-6855.

"Humanized" forms of nonhuman (e.g., murine) antibodies are antibodies that contain minimal sequence derived from nonhuman immunoglobulin. For the most part, humanized antibodies are human immunoglobulins (recipient antibody) in which the native CDR residues are replaced by residues from the corresponding CDR of a nonhuman species (donor antibody) such as mouse, rat, rabbit or nonhuman primate having the desired specificity, affinity, and capacity. In some instances, one or more framework (FW) region residues of the human immunoglobulin are replaced by corresponding nonhuman residues. Furthermore, humanized antibodies may comprise residues that are not found in the recipient antibody or in the donor antibody. These modifications are made to further refine antibody performance. In general, a humanized antibody heavy or light chain will comprise substantially all of at least one or more variable domains, in which all or substantially all of the CDRs correspond to those of a nonhuman immunoglobulin and all or substantially all of the FWs are those of a human immunoglobulin sequence. In certain embodiments, the humanized antibody will comprise at least a portion of an immunoglobulin constant region (Fc), typically that of a human immunoglobulin. See, Jones et al. (1986) Nature 321: 522-525; Riechmann et al., (1988) Nature 332: 323-329; and Presta, (1992) Curr. Op. Struct. Biol. 2: 593-596.

A "human antibody" can be an antibody derived from a human or an antibody obtained from a transgenic organism that has been "engineered" to produce specific human antibodies in response to antigenic challenge and can be produced by any method known in the art. In certain techniques, elements of the human heavy and light chain loci are introduced into strains of the organism derived from embryonic stem cell lines that contain targeted disruptions of the endogenous heavy chain and light chain loci. The transgenic organism can synthesize human antibodies specific for human antigens, and the organism can be used to produce human antibody-secreting hybridomas. A human antibody can also be an antibody wherein the heavy and light chains are encoded by a nucleotide sequence derived from one or more sources of human DNA. A fully human antibody can also be constructed by genetic or chromosomal transfection methods, as well as phage display technology, or in vitro activated B cells, all of which are known in the art.

An "antibody fragment" refers to a part of the full length antibody comprising at least the antigen binding portion of the antibody from which it was derived. Examples of antibody fragments include, but are not limited to, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above.

"Fv" is an antibody fragment that contains a complete antigen-recognition and binding site. This region consists of a dimer of one heavy and one light chain variable domain in tight, non-covalent or covalent association. Three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Bispecific antibodies" are monoclonal, preferably human or humanized, antibodies that have binding specificities for at least two different antigens or at least two different epitopes on the same antigen. In the present case, one of the binding specificities is for EGFR and the other is for any other antigen or for another epitope on EGFR. Bispecific antibodies may also be used to localize cytotoxic agents to cells which express EGFR. These antibodies possess an EGFR-binding arm and an arm which binds the cytotoxic agent. Bispecific antibodies can be prepared as full length antibodies or antibody fragments (e.g. $F(ab')_2$ bispecific antibodies). See, U.S. Pat. No. 8,293,241, incorporated herein by reference in its entirety, for methods for producing bispecific antibodies and details.

An "antigen" refers to one or more molecules of one or more portions of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens. The binding of the antigen to antibody must be above background levels.

An "epitope" refers to the site on a target compound that is capable of being recognized by, and bound by, an antibody. In general, epitopes consist of chemically active surface groupings of molecules, for example, amino acids or sugar side chains, and have specific three-dimensional structural characteristics as well as specific charge characteristics. In the case where the target compound is a protein, for example, an epitope may refer to the amino acids (particularly amino acid side chains) that are bound by the antibody. Overlapping epitopes include at least one common amino acid residue, e.g., at least 2, 3, 4 or 5 common amino acid residues. Epitopes of antibodies can be identified with a cross-blocking assay such as described in *Antibodies, A Laboratory Manual*, Cold Spring Harbor Laboratory, Ed Harlow and David Lane (1988), herein incorporated by reference in its entirety.

A "complementarity determining region (CDR)" refers to amino acid sequences which together define the binding affinity and specificity of the natural Fv region of a native immunoglobulin binding site. The light and heavy chains of an immunoglobulin each have three CDRs. By definition, the CDRs of the light chain are bounded by the residues at positions 26 and 30 (CDR1), 48 and 50 (CDR2), 87 and 92 (CDR3); the CDRs of the heavy chain are bounded by the residues at positions 19 and 26 (CDR1), 44-50 (CDR2), and 89-99 (CDR3), using the numbering convention delineated by Kabat et al., (1991) Sequences of Proteins of Immunological Interest, $5^{th}$ Edition, Department of Health and Human Services, Public Health Service, National Institutes of Health, Bethesda (NIH Publication No. 91-3242), herein incorporated by reference in its entirety.

A "framework region (FR)" refers to amino acid sequences interposed between CDRs.

A "specificity determining residue (SDR)" refers to amino acid residues of an immunoglobulin that is directly involved in antigen contact.

A "constant region" refers to the portion of an antibody molecule which confers effector functions. A light chain constant region can be of the kappa or lamda type. A heavy chain constant region can be selected from any of five isotypes: alpha, delta, epsilon, gamma, or mu. Heavy chains of various subclasses (such as the IgG subclass of heavy chains) are responsible for different effector functions. Thus, by choosing the desired heavy chain constant region, humanized antibodies with the desired effector function can be produced.

"Immunogenicity" refers to a measure of the ability of an antigen to elicit an immune response (humoral or cellular) when administered to a recipient.

"Immunoreactivity" refers to a measure of the ability of an immunoglobulin to recognize and bind to a specific antigen.

"Immunoassay" refers to a test that measures the presence, amount, or concentration of a molecule using an antibody or antibody fragment. Non-limiting examples of immunoassays include immunohistochemistry, immunofluorescence, enzyme-linked immunosorbent assays (ELISAs), enzyme immunoassays (EIAs), radioimmunoassays (RIAs), flow cytometry, real-time immunoquantitative polymerase chain reactions (iqPCRs), protein microarrays, surface plasmon resonance, and the CellSearch assays for detecting circulating tumor cells.

"Substantially Similar Binding Properties" is a term used to describe an aspect of this invention. In one embodiment, an antibody having at least one amino acid change as compared to a parent antibody, such as a humanized antibody, is encompassed. The antibody having a change from a parent antibody must have "substantially similar binding properties" as compared to the parent antibody. This means that the antibody having a change retains the ability to preferentially bind an antigen recognized by the parent antibody used to produce the derivative antibody. Preferably, the affinity of an antibody having an amino acid change or changes, such as a humanized antibody, has at least about 10% of the affinity of the parent antibody, more preferably at least about 25%, even more preferably at least about 50%. Most preferably, such an antibody exhibits an antigen-binding affinity that is at least about 75% of the affinity of the parent antibody. Methods for assaying antigen-binding affinity are known in the art and include half-maximal binding assays, competition assays, and Scatchard analysis. In a preferred aspect, antigen-binding affinity is assayed using a competition assay.

"Substantially Homologous" refers to an antibody sequences that exhibits at least about 85% identity, at least about 90% identity, or at least about 95% identity with a reference antibody sequence, or wherein the sequence of an antibody fragment exhibits at least about 85% identity, at least about 90% identity, or at least about 95% identity with the corresponding fragment from a reference antibody sequence, where percent identity is determined by comparing the number of identical amino acid residues between the two antibodies or antibody fragments, where the positions of the amino acid residues are indicated, such as by using the Kabat numbering scheme.

"Substantially pure" describes a homogeneous preparation of an antibody or antibody fragment, or other chemical or biological agents. Substantially pure of at least 80%, at least about 90%, at least about 95%, at least about 98%, and at least about 99% are encompassed.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

A "EGFR-associated disorder" is any disorder in which EGFR contributes to etiology or a disorder whose condition, symptoms, or risk of onset is altered by provision of a EGFR blocking agent.

An "EGFR ligand" refers to a polypeptide that binds to and/or activates EGFR. The term includes membrane-bound precursor forms of the EGFR ligand, as well as proteolytically processed soluble forms of the EGFR ligand.

Unless otherwise defined, all technical and scientific terms used herein have the same meaning as commonly understood by one of ordinary skill in the art to which this present invention belongs. Although methods and materials similar or equivalent to those described herein can be used in the practice or testing described herein, suitable methods and materials are described below. In addition, embodiments of the present invention described with respect to Chothia CDRs may also be implemented using Kabat CDRs.

All publications, patent applications, patents, and other references mentioned herein are incorporated by reference in their entirety. In addition, the materials, methods, and examples are illustrative only and not intended to be limiting.

Anti-EGFR Antibodies and Antibody Fragments

In one embodiment, the invention provides an isolated antibody, where the antibody binds EGFR with high sensitivity, high specificity and high affinity. The antibodies and antibody fragments described herein are capable of modulating the activity and/or function of EGFR.

In one embodiment, the isolated antibody comprises:

a) an antibody light chain variable region comprising:

i. QGISNN for CDR1;  (SEQ ID NO: 3)

ii. DAS for CDR2;  (SEQ ID NO: 4)
    and iii. LQHRYLPVH for CDR3;  (SEQ ID NO: 5)

and b) an antibody heavy chain variable region comprising:

i. GFSLSTSGMG for CDR1;  (SEQ ID NO: 6)

ii. IWWDDDK for CDR2;  (SEQ ID NO: 7)
    and iii. ARMGMTGYFDF for CDR3.  (SEQ ID NO: 8)

In other embodiments, an isolated antibody or antibody fragment is encompassed, where the antibody comprises a light chain variable domain sequence, wherein the light chain variable domain sequence comprises at least one, two, or three of the following sequences within a CDR region:

QGISNN,  (SEQ ID NO: 3)

DAS,  (SEQ ID NO: 4)

LQHRYLPVH.  (SEQ ID NO: 5)

The CDR regions may have an amino acid sequence that differs by no more than 4, 3, 2, or 1 amino acids (e.g., substitutions, insertions or deletions) for every 10 amino acids.

Also encompassed is an isolated antibody or antibody fragment, wherein the antibody or antibody fragment comprises a heavy chain variable domain sequence, wherein the heavy chain variable domain sequence comprises at least one, two, or three of the following sequences within a CDR region:

GFSLSTSGMG,  (SEQ ID NO: 6)

IWWDDDK,  (SEQ ID NO: 7)

ARMGMTGYFDF.  (SEQ ID NO: 8)

The CDR regions may have an amino acid sequence that differs by no more than 4, 3, 2, or 1 amino acids (e.g., substitutions, insertions or deletions) for every 10 amino acids.

In other embodiments, an isolated antibody or antibody fragment is encompassed, where the antibody comprises a light chain variable domain sequence and a heavy chain variable domain sequence, wherein the light chain variable domain sequence comprises at least one, two, or three of the following sequences within a CDR region:

QGISNN,  (SEQ ID NO: 3)

DAS,  (SEQ ID NO: 4)

LQHRYLPVH,  (SEQ ID NO: 5)

wherein the CDR regions may have an amino acid sequence that differs by no more than 4, 3, 2, or 1 amino acids (e.g., substitutions, insertions or deletions) for every 10 amino acids; and the heavy chain variable domain sequence comprises at least one, two, or three of the following sequences within a CDR region:

GFSLSTSGMG,  (SEQ ID NO: 6)

IWWDDDK,  (SEQ ID NO: 7)

ARMGMTGYFDF,  (SEQ ID NO: 8)

wherein the CDR regions may have an amino acid sequence that differs by no more than 4, 3, 2, or 1 amino acids (e.g., substitutions, insertions or deletions) for every 10 amino acids relative to a sequence listed above.

In some embodiments, an isolated antibody comprising all six CDRs disclosed herein, or closely related CDRs, e.g., CDRs which are identical or which have a least one amino acid alteration, but not more than two, three or four alterations (e.g., substitutions, deletions, or insertions) is encompassed.

The invention also provides an isolated antibody comprising in its epitope binding domain one or more CDR sequences chosen from:

i. QGISNN,  (SEQ ID NO: 3)

ii. DAS,  (SEQ ID NO: 4)

iii. LQHRYLPVH,  (SEQ ID NO: 5)

iv. GFSLSTSGMG,  (SEQ ID NO: 6)

-continued v. IWWDDDK, (SEQ ID NO: 7)
and vi. ARMGMTGYFDF, (SEQ ID NO: 8)

The antibodies according to the invention include, in addition, antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), betabranched side chains (e.g., threonine, valine, isoleucine) and aromatic side chains (e.g., tyrosine, phenylalanine, tryptophan, histidine). Thus, a predicted nonessential amino acid residue in an anti-EGFR antibody can be, for example, replaced with another amino acid residue from the same side chain family.

Equivalent amino acids can be determined by their structural homology with the substituent amino acid or on the results of comparative tests of functionality between the various antibodies likely to be generated. The table below summarizes non-limiting examples of possible amino acid substitution that can be made to the amino acid sequence of the disclosed anti-EGFR sequence without producing significant changes to the functionality of the resulting modified antibody; inverse substitutions are also possible.

| Original Residue | Possible amino acid substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

In some embodiments, an isolated antibody comprising a light chain comprising the amino acids of SEQ ID NO: 1 is encompassed. In some embodiments, an isolated antibody comprising a heavy chain comprising the amino acids of SEQ ID NO: 2 is encompassed. In some embodiments, an isolated antibody comprising a light chain comprising the amino acids of SEQ ID NO: 1 and a heavy chain comprising the amino acids of SEQ ID NO: 2 is encompassed.

The antibodies of the invention can be chosen from any of: a) a monoclonal antibody; b) a polyclonal antibody; c) a recombinant antibody; d) a chimeric antibody; e) a humanized antibody; f) a human antibody; and g) an antigen-binding fragment or antigen-binding portion of anyone of (a) through (f).

"Antibody fragments," "antibody portions," "antigen-binding fragments," and "antigen-binding portions," are encompassed and comprise a portion of a full length antibody, generally at least the antigen binding portion/domain or the variable region thereof. Examples of antibody fragments include diabodies, single chain antibody molecules, immunotoxins, and multispecific antibodies formed from antibody fragments. In addition, antibody fragments comprise single chain polypeptides having the characteristics of a VH chain binding pathological EGFR, namely being able to assemble together with a VL chain or of a VL chain binding to pathological EGFR, namely being able to assemble together with a VH chain to form a functional antigen binding pocket and thereby providing the property of binding to pathological EGFR. The terms also comprise fragments that per se are not able to provide effector functions (e.g., ADCC/CDC) but provide this function after being combined with the appropriate antibody constant domain(s).

The term "effector functions" includes, but is not limited to, C1q binding; complement dependent cytotoxicity (CDC); Fc receptor binding; antibody-dependent cell-mediated cytotoxicity (ADCC); phagocytosis; and down regulation of cell surface receptors (e.g. B cell receptor; BCR).

In some embodiments, the light or the heavy chain variable framework (e.g., the region encompassing at least FR1, FR2, FR3, and optionally FR4) can be chosen from: (a) a light or heavy chain variable framework including at least 80%, 90%, 95%, or 100% of the amino acid residues from a human light or heavy chain variable framework, e.g., a light or heavy chain variable framework residue from a human mature antibody, a human germline sequence, a human consensus sequence, or a human antibody described herein; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, a human consensus sequence; (c) a non-human framework (e.g., a rodent framework); or (d) a non-human framework that has been modified, e.g., to remove antigenic or cytotoxic determinants, e.g., deimmunized, or partially humanized.

In some embodiments, the antibody or antibody fragment includes at least one non-human CDR. In various embodiments, the antibody or antibody fragment includes one, two, three, four, five, or six such non-human CDR's and includes at least one amino acid difference in at least three of HC FR1, HC FR2, HC FR3, LC FR1, LC FR2, and LC FR3.

In some embodiments, the light or heavy chain variable domain sequence of the antibody or antibody fragment includes an amino acid sequence, which is at least 80%, 85%, 90%, 95%, 97%, 98%, 99% or more identical to a variable domain sequence disclosed herein; or which differs by at least 1 or 5 residues, but less than 40, 30, 20, or residues, from a variable domain sequence disclosed herein.

In some embodiments, one or both of the variable domains include amino acid positions in the framework region that are variously derived from both a murine antibody and a humanized antibody or germline sequence. For example, the variable domain will include a number of positions at which the amino acid is identical to both the murine antibody and the human antibody (or germline sequence) because the two are identical at that position. Of the remaining framework positions where the murine and human differ, at least 50, 60, 70, 80, or 90% of the positions of the variable domain are preferably identical to the human antibody (or germline sequence) rather than the murine. None, or at least one, two, three, or four of such remaining framework positions may be identical to the murine antibody rather than to the human antibody. For example, in HC FR1, one or two such positions can be murine; in HC FR2, one or two such positions can be murine; in FR3, one, two, three, or four such positions can be murine; in LC FR1, one, two, three, or four such positions can be murine; in LC FR2, one or two such positions can be murine; in LC FR3, one or two such positions can be murine.

In some embodiments, the light or heavy chain variable domain sequence of the antibody or antibody fragment includes an amino acid sequence encoded by a nucleic acid sequence described herein or a nucleic acid that hybridizes to a nucleic acid sequence described herein (e.g., a specific nucleic acid sequence or a nucleic acid sequence that encodes an amino acid sequence described herein) or its complement, e.g., under low stringency, medium stringency, high stringency, or very high stringency conditions.

In one aspect of the invention, the disclosed antibodies and antibody fragments are capable of binding to different parts of EGFR and to different forms of EGFR. In some embodiments, the antibodies and antibody fragments bind to the extracellular domain of EGFR. In various embodiments, the antibodies and antibody fragments bind to the soluble form of EGFR. In some embodiments, the antibodies and antibody fragments bind to the membrane-associated form of EGFR. In some embodiments, the antibodies and antibody fragments bind to the membrane-bound form of EGFR. In other embodiments, the antibodies and antibody fragments bind to the dimerized form of EGFR. In further embodiments, the dimerized form of EGFR is a homodimer. In other embodiments, the dimerized form of EGFR is a heterodimer. In some embodiments, the antibodies and antibody fragments bind to an unphosphorylated form of EGFR. In other embodiments, the antibodies and antibody fragments binds to a phosphorylated form of EGFR. In some embodiments, the antibodies and antibody fragments bind to a non-phosphorylated form of EGFR.

EGFR heterodimers include, but are not limited to, EGFR-ErbB2, EGFR-ErbB3, and EGFR-ErbB4 heterodimers.

As used herein, a membrane-associated protein is a protein that can be found localized with a membrane upon examination of cell. A membrane-bound protein is one that interfaces at least in part with the lipid bilayer. In some aspects, it is bound to the membrane via ionic interactions. In other aspects, a membrane-bound protein is bound to the membrane via covalent interactions. In various aspects, a membrane bound protein is bound to the membrane via hydrophobic interactions.

In some embodiments, the antibodies or antibody fragments disclosed herein include those specific or preferentially selective for a soluble form of EGFR. In some embodiments, the EGFR is shed. The soluble EGFR protein can be an extracellular domain of EGFR. The soluble EGFR protein can be phosphorylated. The soluble EGFR of the present invention can be part of a cell fragment or in any non-cellular lipid bilayer. In some embodiments, a soluble or shed EGFR of the present invention is phosphorylated.

The present invention discloses antibodies and antibody fragments capable of binding to EGFR with high sensitivity, high specificity and high affinity with a specific affinity of between $10^{-8}$ and $10^{-11}$ M. In some embodiments, an antibody or antibody fragment binds EGFR or a particular form of EGFR such as a soluble form or a membrane-bound form with a specific affinity of greater than $10^{-7}$ M, $10^{-8}$ M, $10^{-9}$ M, $10^{-10}$ M, or $10^{-11}$ M, or an affinity between $10^{-8}$ M-$10^{-11}$ M, $10^{-9}$ M-$10^{-10}$ m and $10^{-10}$ M-$10^{-11}$ M.

In an aspect of the present invention, preferential binding is relative to background non-specific binding. In another aspect, the preferential binding is at least 2-fold, 3-fold, 4-fold, 5-fold, 10-fold, 100-fold, 1.000-fold, 10.000-fold or 1,000,000-fold relative to background non-specific binding. Methods for assaying antigen-binding affinity are known in the art and include half-maximal binding assays, competition assays, and Scatchard analysis, as set forth in Ausubel et al., Current Protocols in Molecular Biology (John Wiley & Sons Inc.). A binding of the antibody can be measured in any way, such as a gel-shift assay. The binding properties of an antibody may be measured by any standard method, e.g., one of the following methods: BIACORE™ analysis, Enzyme Linked Immunosorbent Assay (ELISA), Fluorescence Resonance Energy Transfer (FRET), x-ray crystallography, sequence analysis and scanning mutagenesis. The ability of a protein to inhibit one or more activities of EGFR can be evaluated in vitro or in an animal model of a disorder, e.g., a disorder described herein. Preferably, the antibody has a statistically significant effect that indicates that the antibody inhibits one or more activities of EGFR.

The binding interaction of a protein of interest (EGFR) and a target (e.g., EGFR ligand) can be analyzed using surface plasmon resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63: 2338-2345; Szabo et al. (1995) *Curr. Opin. Struct. Biol.* 5: 699-705 and online resources provide by Biacore International AB (Uppsala, Sweden). Information from SPR can be used to provide an accurate and quantitative measure of the equilibrium dissociation constant ($K_d$), and kinetic parameters, including $K_{on}$ and $K_{off}$, for the binding of a biomolecule to a target.

Epitopes can also be directly mapped by assessing the ability of different antibodies to compete with each other for binding to EGFR using BIAcore chromatographic techniques (Pharmacia BIAtechnology Handbook, "Epitope Mapping", Section 6.3.2, (May 1994); see also Johne et al. (1993) *J. Immunol. Methods,* 160: 191-198). Additional general guidance for evaluating antibodies, e.g., in Western blots and immunoprecipitation assays, can be found in *Antibodies: A Laboratory Manual,* ed. by Harlow and Lane, Cold Spring Harbor press (1988)).

In one aspect of the present invention, the antibody is an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody. For example, the antibody is in a composition that includes less than 20 other species of anti-EGFR antibodies, e.g., in a composition that does not include another species of anti-EGFR antibody.

In some embodiments, the antibody can be humanized. Preferably, the antibody or antibody fragment does not evoke a neutralizing antibody response, e.g., the human anti-murine antibody (HAMA) response. HAMA can be problematic in a number of circumstances, e.g., if the antibodies are desired to be administered repeatedly, e.g., in treatment of a chronic or recurrent disease condition. A HAMA response can make repeated antibody administration potentially ineffective because of an increased antibody clearance from the serum and also because of potential allergic reactions. See Saleh et al., (1990) Cancer Immunol. Immunother. 32:180-190; LoBuglio et al. (1986) *Hybridoma*, 5: 5117-5123.

For example, the antibody can be a human, humanized, CDR-grafted, chimeric, mutated, affinity matured, deimmunized, synthetic or otherwise in vitro-generated antibody, and combinations thereof. In one embodiment, the anti-EGFR antibody is a humanized antibody.

The heavy and light chains of the anti-EGFR antibody can be substantially full-length. The antibody or antibody fragment can include at least one, and preferably two, complete heavy chains, and at least one, and preferably two, complete light chains or can include an antigen-binding fragment (e.g., a Fab, F(ab')$_2$, Fv or a single chain Fv fragment). In yet other embodiments, the antibody or antibody fragment has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody or antibody fragment has a light chain constant region chosen from, e.g., kappa or lambda, particularly, kappa (e.g., human kappa).

In one aspect of the present invention, the anti-EGFR antibody can be gylocosylated. In some embodiments, the glycosylation includes modification by oligosaccharides. In some embodiments, the oligosaccharides are modified. In one embodiment the modified oligosaccharides have reduced fucosylation as compared to non-modified oligosaccharides. In other embodiments, the modified oligosaccharides are hybrid or complex. In a further embodiment, the anti-EGFR antibody has an increased proportion of nonfucosylated oligosaccharides or bisected, nonfucosylated oligosaccharides in the Fc region of said molecule. In one embodiment, the bisected, nonfucosylated oligosaccharides are hybrid. In a further embodiment, the bisected, nonfucosylated oligosaccharides are complex. In a one embodiment, at least 20% of the oligosaccharides in the Fc region of said polypeptide are nonfucosylated or bisected, nonfucosylated. In more preferred embodiments, at least 30%, 35%, 40%, 45%, 50%, 55%, 60%, 65%, 70% or 75% or more of the oligosaccharides are nonfucosylated or bisected, nonfucosylated.

In another aspect, the anti-EGFR antibody or antibody fragment can be derivatized or linked to another functional molecule, e.g., another peptide, protein, or compound. For example, the antibody can be functionally linked (e.g., by chemical coupling, genetic fusion, non-covalent association or otherwise) to one or more other molecular entities, such as another antibody (e.g., a bispecific or a multi-specific antibody), toxins, radioisotopes, polymers, cytotoxic or cytostatic agents, among others.

In some embodiments, the anti-EGFR antibody or antibody fragment is linked to an imaging agent or a therapeutic agent selected from the group consisting of: imaging agent; cytotoxic agent; angiogenesis inhibitors; kinase inhibitors; co-stimulation molecule blockers; adhesion molecule blockers, anti-cytokine antibody or functional fragment thereof; an anticancer drug; methotrexate; cyclosporine; rapamycin; FK506; detectable label or reporter; a TNF antagonist; an antirheumatic; a muscle relaxant; a narcotic; a non-steroid anti-inflammatory drug (NSAID); an analgesic; an anesthetic; a sedative; a neuromuscular blocker; an antimicrobial; a corticosteroid; an anabolic steroid; an erythropoietin; an immunization; an immunosuppressive; a hormone replacement drug; a cytokine; a cytokine analog; and an anti-EGFR antibody or antibody fragment.

In some embodiments, the anti-EGFR antibody is conjugated to a virus or viral-like particle. In some embodiments, the anti-EGFR antibody is conjugated to a liposome or lipid-based particle.

In one aspect, the anti-EGFR antibody or antibody fragment is capable of modulating the activity and/or function of EGFR. In some embodiments, the anti-EGFR antibody or antibody fragment is capable of reducing the activity of EGFR. In other embodiments, the anti-EGFR antibody or antibody fragment is capable of increasing the activity of EGFR. In other embodiments, the anti-EGFR antibody or antibody fragment modulates the activity of soluble form of EGFR; a membrane-bound form of EGFR; a monomer of EGFR; a homodimer form of EGFR; a heterodimer form of EGFR; or a phosphorylated form of EGFR.

Antibody Production

Method for producing the antibodies and antibody fragments of the present invention are encompassed. In one embodiment the method comprises culturing a cell producing the anti-EGFR antibody and isolating the antibody. Alternatively, antibodies can be made, for example, by preparing and expressing synthetic genes that encode the recited amino acid sequences or by mutating human germline genes to provide a gene that encodes the recited amino acid sequences. Moreover, these antibodies and other anti-EGFR antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228: 1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667,988; and 5,885,793.

In addition to the use of display libraries, other methods can be used to obtain a EGFR binding antibody. For example, the EGFR protein or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. In some embodiments, EGFR-binding antibodies are expressed by a cell line. Using the hybridoma technology, antigen-specific monoclonal antibodies derived from the genes with the desired specificity may be produced and selected. See, e.g., XENOMOUSE™, Green et al. (1994) Nature Genetics 7: 13-21, U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR-grafting method that may be used to prepare humanized antibodies described herein (U.S. Pat. No. 5,225, 539). All or some of the CDRs of a particular human antibody may be replaced with at least a portion of a non-human antibody. It may only be necessary to replace the CDRs required for binding or binding determinants of such CDRs to arrive at a useful humanized antibody that binds to EGFR.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) Science 229: 1202-1207; by Oi et al. (1986) BioTechniques 4: 214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al. (1992) J. Mol. Biol. 227:776-798; Cook, G. P. et al. (1995) Immunol. Today 16: 237-242; Chothia, D. et al. (1992) J. Mol. Bio. 227:799-817; and Tomlinson et al. (1995) EMBO J. 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

A non-human EGFR-binding antibody may also be modified by specific deletion of human T cell epitopes or "deimmunization" by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made. Conservative substitutions involve replacing amino acids with those that have similar charge or hydrophobicity, for example:

(1) non-polar: Ala (A), Val (V), Leu (L), Ile (I), Pro (P), Phe (F), Trp (W), Met (M);
(2) uncharged polar: Gly (G), Ser (S), Thr (T), Cys (C), Tyr (Y), Asn (N), Gln (Q);
(3) acidic: Asp (D), Glu (E);
(4) basic: Lys (K), Arg (R), His (H).

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Often, but not exclusively, an amino acid common to a position in human germline antibody sequences may be used. After the deimmunizing changes are identified, nucleic acids encoding VH and VL can be constructed by mutagenesis or other synthetic methods (e.g., de novo synthesis, cassette replacement, and so forth). A mutagenized variable sequence can, optionally, be fused to a human constant region, e.g., human IgG1 or kappa constant regions.

In some cases, a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs can be eliminated by substitutions outside the CDRs. In some cases, an alteration within a CDR is the only option, and thus variants with and without this substitution can be tested. In other cases, the substitution required to remove a potential T cell epitope is at a residue position within the framework that might be critical for antibody binding. In these cases, variants with and without this substitution are tested. Thus, in some cases several variant deimmunized heavy and light chain variable regions are designed and various heavy/light chain combinations are tested to identify the optimal deimmunized antibody. The choice of the final deimmunized antibody can then be made by considering the binding affinity of the different variants in conjunction with the extent of deimmunization, particularly, the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; 5,530,101; and 6,407,213; Tempest et al. (1991) Biotechnology 9:266-271. Still another method is termed "humaneering" and is described, for example, in U.S. 2005-008625.

The antibody disclosed herein can include a human Fc region, e.g., a wild-type Fc region or an Fc region that includes one or more alterations. In one embodiment, the constant region is altered (e.g., mutated) to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) Mol. Immunol. 30:105-08). See also, e.g., U.S. 2005-0037000.

In some embodiments, an anti-EGFR antibody is modified, e.g., by mutagenesis, to provide a pool of modified antibodies. The modified antibodies are then evaluated to identify one or more antibodies which have altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In some embodiments, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In some embodiments, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) CRC Crit. Rev. Biochem. 22:259-306. Removal of any carbohydrate moieties present on the antibodies may be accomplished chemically or enzymatically as described in the art. See Hakimuddin et al. (1987) Arch. Biochem. Biophys. 259: 52; Edge et al. (1981) Anal. Biochem. 118: 131; and Thotakura et al. (1987) Meth. Enzymol. 138:350); U.S. Pat. No. 5,869,046 for a modification that increases in vivo half-life by providing a salvage receptor binding epitope.

In some embodiments, an antibody has CDR sequences that differ only insubstantially from those disclosed herein. Insubstantial differences include minor amino acid changes, such as substitutions of 1 or 2 out of any of typically 5-7 amino acids in the sequence of a CDR, e.g., a Chothia or Kabat CDR. Typically an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J. Immun. 147:2657-62; Morgan et al. (1995) Immunology 86:319-24), or changing the species from which the constant region is derived.

The anti-EGFR antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) Protein Eng. 9(6): 531-7.

In another aspect, the present invention includes a nucleic acid molecules encoding the antibodies described herein. Vectors comprising these nucleic acid molecules and host cells comprising the vectors are also encompassed. Such nucleic acid molecule can be integrated into the genome of the host cell or can be present on a vector such as a plasmid or viral vector. A nucleic acid molecule of the present invention may be transiently present in such a host cell. In some embodiments, a host cell is selected from the group consisting of *E. coli; Bacilli*, (e.g., *Bacillus subtilis*); enterobacteriacae (e.g., *Salmonella, Serratia* and *Pseudomonas*); yeast (e.g., *Saccharomyces; Pichia pastoris*); Sf9 insect cells; Sp2/0 cells; VERO cells; HeLa cells; Chinese hamster ovary (CHO) cells; W138 cells; BHK cells; COS-7 cells; and MDCK cells. In other embodiments, a host cell is selected from a breast cancer cell line such as SKBR3, MCF-7, MDA-MB-231, MDA-MB-435, and ZR75B. In another aspect, a host cell is selected from a prostate cancer cell line such as PC3, DU145 and LNCap. In other embodiments, a host cell is selected from a colon cancer cell line such as HT-29. In further embodiments, a host cell is selected from a skin cancer cell line such as A431. In various embodiments, a host cell is selected from a kidney cancer cell line such as BHK-21 or COS-7. In other embodiments, a host cell is selected from an ovarian cancer cell line such as A2780, A2780ADR, or A2780cis. In one embodiment, it is a CHO cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced.

In an exemplary system for antibody expression, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformed host cells are cultured to allow for expression of the antibody heavy and light chains and the antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) Adv. Immunol. 51:1-84; Jefferis et al. (1998) Immunol. Rev. 163:59-76). In one embodiment, the Fc domain is produced in a mammalian expression system that appropriately glycosylates the residue corresponding to asparagine 297. The Fc domain or other region of the antibody can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Diagnostic Methods, Assays, and Kits

In a further aspect, the present invention encompasses immunoassays for detecting EGFR and for diagnosing EGFR-related diseases, utilizing an antibody or antibody fragment of the present invention.

In one embodiment, an immunoassay for detecting EGFR is encompassed. In some embodiments, the immunoassay comprises: (a) contacting a sample with an effective binding amount of one of the antibodies or antibody fragments of the present invention; and (b) detecting EGFR quantitatively or qualitatively by analyzing the binding of the antibody to EGFR.

One aspect of the present invention includes a method of detecting cancer cells expressing EGFR, particularly cancers of the lung, ovary, colon, colorectum, prostate, breast, head and neck, skin, stomach, pancreas and immune system, by detecting EGFR with an antibody or antibody fragment of the present invention. Another aspect of the present invention includes a method of diagnosing colon cancer by detecting EGFR with an antibody or antibody fragment of the present invention.

Methods of detecting cells expressing EGFR may involve biological samples such as a cell or tissue selected from the breast, ovary, cervix, prostate, colon, stomach, kidney, liver, head, neck, lung, blood, pancreas, skin, testis, thyroid, and/or brain. Samples may include samples of blood, plasma, urine, serum, tissue, and/or cells.

Kits comprising the antibodies of the invention are encompassed and can include frozen or lyophilized antibodies or antibody fragments to be reconstituted by thawing or by suspension in a liquid vehicle. The kits can also include a carrier or buffer. Preferably, the kit also comprises instructions for reconstituting and using the antibody. The kit employing antibodies, including chimeric and humanized antibodies of the present invention, can be used for immunohistochemical evaluation of cancers, including cancer of the breast, ovary, cervix, prostate, colon, stomach, kidney, liver, head, neck, lung, blood, pancreas, skin, testicle, thyroid and brain, most preferentially human breast, ovary, head, neck, and brain, and in particular human breast cells.

Kits, including the reagents necessary for immunohistochemical analysis can be provided as follows: (a) anti-EGFR antibody or antibody fragment of the present invention, or chimeric or humanized variants thereof; (b) blocking reagent (in the form of, for example, goat serum) and secondary antibody (such as, for example, goat anti-mouse antibody); (c) detectable marker (such as, for example, immunoperoxidase or alkaline phosphatase); and (d) developing reagents. The primary antibody (anti-EGFR antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

In a further aspect, the present invention provides a kit for the detection of EGFR comprising: (a) an antibody or antibody fragment of the present invention; and (b) a secondary antibody conjugated to a detectable label. The kit may be used for to detect EGFR in any type of immunoassay, such as, immunohistochemistry, immunofluorescence, ELISA, and circulating tumor cell assay.

In some embodiments, the kit for the detection of EGFR comprises: (a) a monoclonal antibody having one or more of the light chain CDR antigen binding site amino acid sequences set forth in FIG. 1B, and one or more of the heavy chain CDR antigen binding site amino acid sequences set forth in FIG. 1B; and (b) a secondary antibody conjugated to a detectable label.

Kits can include reagents for assaying a sample containing EGFR, where such kits may include: EGFR-specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of EGFR in a sample; instructions; and the like.

In further aspect, the present invention provides a method for diagnosing an EGFR-related disorder such as cancer in humans comprising: (a) removing a specimen from a patient suspected of having a cancer; (b) contacting the specimen with a labeled or non-labeled antibody or antibody fragment of the present invention; (c) optionally adding a detectable label that is specific to the antibody of step (b); (d) detecting the presence or absence of the antigen-antibody complex; and (e) diagnosing an EGFR-related disorder such as cancer if the antigen-antibody complex is detected. Such a method of diagnosing cancer can be performed in vivo or in vitro.

In a still further aspects, the present invention provides a method for diagnosing cancer in humans comprising: (a) removing a specimen from a patient suspected of having a cancer; (b) contacting the specimen with a monoclonal antibody having one or more of the light chain CDR antigen binding site amino acid sequences set forth in FIG. 1B, and one or more of the heavy chain CDR antigen binding site amino acid sequences set forth in FIG. 1B; (c) optionally adding a detectable label that is specific to the antibody of step (b); (d) detecting the presence or absence of the antigen-antibody complex; and (e) diagnosing an EGFR-related disorder such as cancer if the antigen-antibody complex is detected. The method of diagnosing cancer can be performed in vivo or in vitro.

In a still further aspect, the present invention provides a method for diagnosing cancer in humans comprising: (a) removing a specimen from a patient suspected of having a cancer; (b) contacting the specimen with a monoclonal antibody comprising the light chain nucleotide sequences set forth in FIG. 2, and the heavy chain nucleotide sequences set forth in FIG. 3; (c) labeling the specimen; and (d) detecting the presence of the antigen-antibody complex by the label. The method of diagnosing cancer can be performed in vivo or in vitro.

The cancers being diagnosed include, but are not limited to, those that are selected from the group consisting of epithelial tumors of the lung, colon, colorectum, ovary, prostate, breast, head and neck, brain, skin, stomach, pancreas, intestines and immune system.

Another aspect of the invention provides an immunohistochemical method for detecting a disease in a subject in which the disease is characterized by the expression of gene products of HER1 and homologues thereof, comprising the steps of: (a) obtaining a tissue specimen, (b) contacting said tissue specimen with an antibody capable of binding to EGFR, (c) staining said tissue specimen with an immunohistochemical stain; and (d) quantitatively or qualitatively detecting the antibody, wherein detection of the antibody indicates the presence of disease in a patient that is characterized by the expression of gene products of HER1 and homologues thereof. In some embodiments, the disease is cancer of the lung, colon, colorectum, ovary, prostate, breast, head and neck, brain, skin, stomach, pancreas, intestines and immune system. The antibody may comprise the full length or fragments of the amino acid sequences in FIG. 1 or the full or partial nucleotide sequences in FIG. 2 and FIG. 3. In various embodiments, an antibody capable of binding to EGFR can be derived based on the information in FIGS. 1-3 according to skill in the art. In further embodiments, said tissue specimen is from a human subject. In other embodiments, the immunohistochemical staining is any staining method known in the art, including but not limited to, hematoxylin and eosin (H&E) staining and silver staining.

An antibody or antibody fragment of the present invention can also be used in diagnosis of diseases characterized by the expression of EGFR, such as cancer. For example, in vivo diagnosis and imaging of cancer of the lung, colon, colorectum, breast, head, neck, brain, skin, stomach, pancreas, intestines and immune system and combinations thereof, most preferentially cancer of the lung, breast and colon and combinations thereof, and cancerous cells that expresses EGFR can be performed in accordance with the methods of the invention. An antibody or antibody fragment of the present invention can also be used for diagnosis in vitro, for example, by using an antibody or antibody fragment disclosed herein to detect the presence of the cancer marker EGFR in a fluid or tissue sample.

Antibodies and antibody fragments can be used in immunoassays to screen body fluids, such as serum, sputum, effusions, urine, cerebrospinal fluid, and the like, for the presence of EGFR. Antibodies and antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

An EGFR-specific antibody or antibody fragment, which can include any or all of the antibodies or antibody fragments specific for HER1-related gene products, and/or chimeric, such as humanized, or other variants thereof, can be used therapeutically, or in developing and performing assays, in vivo or in vitro diagnostic procedures, and imaging. The antibodies can be used alone or in combination with a pharmaceutically-acceptable or diagnostic carrier formulation. EGFR-specific antibodies or antibody fragments can be incorporated into a pharmaceutically or diagnostically acceptable, sterile carrier as a suspension or solution. They can be used as separately administered compositions or given in conjunction with chemotherapeutic agents, immunosuppressive agents, and/or diagnostic agents.

The present invention includes therapeutic and diagnostic compositions comprising an antibody or antibody fragment of the present invention in combination with a pharmaceutically acceptable excipient, diluent or carrier. The present invention also includes a process for preparation of a therapeutic or diagnostic composition comprising admixing an antibody molecule of the present invention together with a pharmaceutically acceptable excipient, diluent or carrier. An antibody molecule can be the sole active ingredient in the therapeutic or diagnostic composition, or can be accompanied by other active ingredients including other antibody ingredients, such as anti-T cell, anti-IFNγ or anti-LPS antibodies, or non-antibody ingredients such as xanthines. Compositions can be incorporated into kits for diagnosing or treating diseases characterized by the expression of EGFR, including, without limitation, cancers of the lung, colon, colorectum, breast, head, neck, brain, skin, stomach, pancreas, intestines and immune system, and combinations thereof.

Antibodies or antibody fragments of the present invention are useful for immunoassays which detect or quantitate levels of EGFR or number of cells bearing EGFR in a sample. Such an immunoassay typically comprises incubating a biological sample from a subject with a need thereof in the presence of a detectably labeled antibody of the present invention capable of identifying the EGFR antigen, and detecting the labeled antibody which is bound in a sample.

In an aspect of the present invention the level, localization of one or more forms of EGFR, including EGFR, can determine, confirm or indicate the status of a cell, collection of cells, or sample from a subject in need thereof. As used herein, "confirm" means that based on the level, localization or both of one or more forms of EGFR, including EGFR, in a cell, collection of cells or sample, or subject provides a sufficient basis to characterize the status of a cell, collection of cells, sample, or subject. As used herein, "confirm" means that based on the level, localization or both of one or more forms of EGFR, including EGFR, in a cell, collection of cells, sample, or subject provides in combination with other analysis a basis to characterize the status of a cell, collection of cells, sample, or subject. As used herein, "indicate" means that based on the level, localization or both of one or more forms of EGFR, including EGFR, in a cell, collection of cells, sample, or subject provides that more likely than not or greater probability of determining the status of a cell, collection of cells, sample or subject is of a particular status.

In one aspect of the present invention, the observation of EGFR distribution can be used to detect the stages associated with a particular disease, for example, breast cancer. The tissue specimens can be incubated with anti-EGFR antibody or antibody fragment, and the resultant EGFR protein-EGFR-specific antibody complex can be detected using standard immune-detection methods.

In some embodiments of the present invention, immunohistochemical staining of EGFR protein-EGFR-specific antibody complex can indicate different stages of cancer.

In one aspect, the EGFR antibody or antibody fragment can be used to detect various stages of EGFR-related disorders.

In some embodiments of the present invention, immunohistochemical staining of EGFR protein-EGFR-specific antibody complex may be used to detect cancer in tissue specimens collected from patients. In various embodiments, detection of certain types of cancer in tissue specimens comprises: (a) obtaining said tissue specimen, (b) contacting said tissue specimen with an antibody or antibody fragment capable of binding to EGFR, and (c) staining said tissue specimen with an immunohistochemical staining. In some embodiments of the invention, the staining indicates the presence of certain types of cancer in said tissue specimen.

In one aspect, a status of a cell or collection of cells can be determined using an antibody of the present invention or of fragment thereof whether that cell, collection of cells, or sample are metastatic tumor cells, non-metastatic tumor cells, from a solid tumor or normal cells. A status of a subject can include whether the analysis provides information on whether a metastatic cancer or non-metastatic tumor is present in the subject.

In an aspect of the present invention, the level, localization or both of one or more forms of EGFR is diagnostic or prognostic of a disease or outcome probability.

In some embodiments, a reduced level of EGFR of a present invention in blood, collection of cells or sample can diagnose, prognose, determine, confirm or indicate that such derived is from a metastatic tissue. In one aspect, "reduced" can mean reduced relative to a control, with the control being a normal cell of the same type that is non-metastatic. In this aspect, the reduction can be greater than 10, 20, 30, 40, 50, 60, 70, 80, 90, 95, or 99%.

In various embodiments, an increased level of EGFR of a present invention in blood, collection of cells or sample can diagnose, prognose, determine, confirm or indicate that such derived is from a metastatic tissue. In one aspect, "increased" can mean increased relative to a control, with the control being a normal cell of the same type that is non-metastatic. In this aspect, the increase can be greater than 10, 20, 30, 40, 50, 60, 70, 80, 90, 95, or 99%.

In an aspect of the present invention, a similar level of EGFR as detected by the antibodies or antibody fragments of the present invention in blood, collection of cells or sample as compared to a normal control can diagnose, prognose, determine, confirm or indicate that such cell was derived from a non-metastatic tissue.

In an aspect of the present invention, a lack of localization of EGFR in a cell nucleus can diagnose, prognose, determine, confirm or indicate that such derived is from a metastatic tissue.

In an aspect of the present invention, localization of EGFR in a cell, collection of cells or sample relative to a normal control can diagnose, prognose, determine, confirm or indicate that such derived from a non-metastatic tissue.

In an aspect of the present invention, the cell, collection of cells or sample is a from the cervix, colon, or breast Antibodies and antibody fragments of the present invention are also useful for immunopathological analysis, such as the differential diagnosis of tumor type, and the subclassification of the tumor based on its expression or localization of at least one form of EGFR, including, without limitation, assessment of metastatic potential, predicted responses to therapy, and overall prognosis.

Anti-EGFR antibodies and antibody fragments permit the definition of subpopulations of tumor cells among the heterogeneous cells present in a growing tumor and can be used, for example, in the typing and cross-matching of the tumor cell "lines", including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy, (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

A biological sample can be treated with nitrocellulose, or other solid support or carrier which is capable of immobilizing cells, cell particles or soluble proteins or glycoproteins. The support can then be washed with suitable buffers followed by treatment with the detectably labeled antibody of the present invention. The solid phase support can then be washed with the buffer a second time to remove unbound antibody. The amount of bound label on the solid support can then be detected by conventional means. The anti-EGFR antibodies of the present invention in complex with a solid support are encompassed.

The antibodies and antibody fragments of the invention can be used in enzyme immunoassays (EIAs) or enzyme-linked immunosorbent assays (ELISAs).

One of the ways in which the antibody or antibody fragment of the present invention can be detectably labeled is by linking to an enzyme. It is also possible to label the antibodies or antibody fragments of the present invention with a fluorescent compound. When the fluorescently labeled antibody or antibody fragment is exposed to light of the proper wave length, its presence can then be detected due to fluorescence. The antibodies or antibody fragments of the present invention also can be detectably labeled by coupling to a chemiluminescent compound. The presence of the chemiluminescently labeled antibody or antibody fragment is then determined by detecting the presence of luminescence that arises during the course of a chemical reaction. A bioluminescent compound can also be used to label the antibodies or antibody fragments of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

In situ detection can be accomplished by removing a specimen from a patient, and providing the labeled antibody or antibody fragment, or the unlabeled antibody or antibody fragment plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In an aspect, an avidin-biotin immunoperoxidase staining system can be used, and a kit utilizing this system is also contemplated, although the methods of the present invention can utilize any suitable staining procedures known in the art.

Certain embodiments include methods of diagnosing or screening an EGFR-related disorder in a subject, or for determining a subject's risk for developing an EGFR-related disorder, by contacting the subject, or a cell, tissue, organ, fluid, or any other sample of the subject, with an effective amount of at least one antibody or antibody fragment; and determining the presence of a complex comprising an EGFR ligand and the antibody or antibody fragment, wherein the presence of the complex is diagnostic for an EGFR-related disorder, or determines that the subject is at risk for developing an EGFR-related disorder. A therapeutic agent may be administered to a subject where an EGFR-related disorder is diagnosed.

Another embodiment includes a method of diagnosing or screening an EGFR-related disorder in a subject, or for determining a subject's risk for developing an EGFR-related disorder, by contacting the subject, or a cell, tissue, organ, fluid, or any other sample of the subject, with an effective amount of at least one antibody or antibody fragment; and determining the presence of a complex comprising an EGFR ligand and the antibody or antibody fragment by measuring the complex using an immunoassay, wherein the presence of the complex is diagnostic for an EGFR-related disorder, or determines that the subject is at risk for developing an EGFR-related disorder. The immunoassay can be any type of immunoassay, including a Western blot, ELISA, immunohistochemistry, or immunofluorescence. A therapeutic agent may be administered to a subject where an EGFR-related disorder is diagnosed.

Another embodiment includes a method of diagnosing or screening an EGFR-related disorder in a subject, or for determining a subject's risk for developing an EGFR-related disorder, by contacting the subject, or a cell, tissue, organ, fluid, or any other sample of the subject, with an effective amount of at least one antibody or antibody fragment; and obtaining a measurement of the presence of a complex comprising an EGFR ligand and the antibody or antibody fragment by measuring the complex using an immunoassay, wherein the presence of the complex is diagnostic of an EGFR-related disorder. The measurement may be obtained by any means, such as by ordering the measurement from a diagnostics vendor, or by receiving measurement from another party. The measurement may be a description of the results of determining the presence of the complex. A therapeutic agent may be administered to a subject where an EGFR-related disorder is diagnosed.

Any suitable detection system can be used in accordance with the methods and kits of the present invention. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present invention, the primary protein signal being amplified is bound anti-EGFR antibody or antibody fragment, which can or cannot be labeled, for example with a protein such as biotin), which is in turn being used to detect a specific target (in the context of the present invention, the target is an EGFR ligand).

Suitable secondary conjugates for use in the methods and kits of the present invention can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody or antibody fragment of the present invention can also be adapted for utilization in an immunometric assay, also known as a "two-site" or "sandwich" assay. In a typical immunometric assay, a quantity of unlabeled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of breast, ovary, cervix, prostate, colon, stomach, kidney, liver, head and neck, lung, blood, pancreas, skin, testicle, thyroid and brain, most preferentially human breast, ovary, head, neck, and brain, in particular human breast cancer and other cancers using the antibodies or antibody fragments of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET).

Anti-EGFR antibodies or antibody fragments can be used in a diagnostic method for detecting the presence of EGFR, in vitro (e.g., a biological sample, such as tissue, biopsy) or in vivo (e.g., in vivo imaging in a subject). For example, human or humanized anti-EGFR antibodies or antibody fragments can be administered to a subject to detect EGFR within the subject. For example, the antibody can be labeled, e.g., with an MRI detectable label or a radiolabel. The subject can be evaluated using a means for detecting the detectable label. For example, the subject can be scanned to evaluate localization of the antibody within the subject. For example, the subject is imaged, e.g., by NMR or other tomographic means.

Examples of labels useful for diagnostic imaging include radiolabels such as $^{131}I$, $^{111}I$, $^{123}I$, $^{99}mTc$, $^{32}P$, $^{33}P$, $^{125}I$, $^{3}H$, $^{14}C$, and $^{188}Rh$; fluorescent labels such as fluorescein and rhodamine; nuclear magnetic resonance active labels; positron emitting isotopes detectable by a positron emission tomography ("PET") scanner; chemiluminescers such as luciferin; and enzymatic markers such as peroxidase or phosphatase. Short range radiation emitters, such as isotopes detectable by short range detector probes, can also be employed. The antibodies or antibody fragments can be labeled with such reagents using known techniques. For example, see Wensel and Meares (1983) Radioimmunoimaging and Radioimmunotherapy, Elsevier, New York for techniques relating to the radiolabeling of antibodies and Colcher et al. (1986) Meth. Enzymol. 121: 802 816.

The subject can be "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pg 65-85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP0 502 814 A. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents, paramagnetic agents (which primarily alter T1) and ferromagnetic or superparamagnetic agents (which primarily alter T2 response). Chelates (e.g., EDTA, DTPA and NTA chelates) can be used to attach (and reduce toxicity) of some paramagnetic substances (e.g., $Fe^{3+}$, $Mn^{2+}$, $Gd^{3+}$). Other agents can be in the form of particles (e.g., less than 10 μm to about 10 nm in diameter). Particles can have ferromagnetic, antiferromagnetic or superparamagnetic properties. Particles can include, but not limited to, magnetite ($Fe_3O_4$), $\gamma$-$Fe_2O_3$, ferrites, and other magnetic mineral compounds of transition elements. Magnetic particles may include one or more magnetic crystals with and without nonmagnetic material. The nonmagnetic material can include synthetic or natural polymers (such as sepharose, dextran, dextrin, starch and the like).

The anti-EGFR antibodies or antibody fragments can also be labeled with an indicating group containing the NMR active $^{19}F$ atom, or a plurality of such atoms inasmuch as (i) substantially all of naturally abundant fluorine atoms are the $^{19}F$ isotope and, thus, substantially all fluorine containing compounds are NMR active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) Scientific American, 246: 78 88 to locate and image EGFR distribution.

In another aspect, the disclosure provides a method for detecting the presence of EGFR in a sample in vitro (e.g., a biological sample, such as serum, plasma, tissue, biopsy). The subject method can be used to diagnose a disorder, e.g., cancer. The method includes: (i) contacting the sample or a control sample with the anti-EGFR antibody or antibody fragment; and (ii) evaluating the sample for the presence of EGFR, e.g., by detecting formation of a complex between the anti-EGFR antibody or antibody fragment and EGFR ligand, or by detecting the presence of the antibody or antibody fragment, or EGFR. For example, the antibody or antibody fragment can be immobilized, e.g., on a support, and retention of the antigen on the support is detected, and/or vice versa. A control sample can be included. A statistically significant change in the formation of the complex in the sample relative to the control sample can be indicative of the presence of EGFR in the sample. Generally, an anti-EGFR antibody or antibody fragment can be used in applications that include fluorescence polarization, microscopy, ELISA, centrifugation, chromatography, and cell sorting (e.g., fluorescence activated cell sorting).

Pharmaceutical Compositions, Uses, and Methods of Treatment

In an additional aspect, the present invention related to methods of treatment using the anti-EGFR antibodies of the present invention, or humanized or deimmunized variants thereof.

The term "subject" as used herein refers to any subject in need thereof, preferably a human patient or subject.

Approximately 30% of epithelial malignancies express EGFR. EGFR-related malignancies include cancers of the lung, colon, rectum, ovary, prostate, breast, head and neck, brain, skin, stomach, pancreas, intestines, and immune system. In one aspect, the present invention discloses the use of anti-EGFR antibodies or antibody fragments to treat EGFR-related disorders. In some embodiments, the anti-EGFR antibody or antibody fragment (e.g., a pharmaceutical composition thereof) is administered to a subject who needs an anti-EGFR antibody therapy or whose condition would be ameliorated by the antibody or antibody fragment. For example, the anti-EGFR antibody can be administered to a subject who has or is at risk for colorectal cancer, or other disorder described herein. In some embodiments, an anti-EGFR antibody described herein is used for the preparation of a medicament for the treatment of colorectal cancer, or other disorder described herein.

In one aspect, the present invention relates to methods for selectively killing tumor cells expressing EGFR. In some embodiments, the method comprises (a) the anti-EGFR antibody or antibody fragment conjugated to a toxin polypeptide to form an immunoconjugate; and (b) reacting the immunoconjugate with said tumor cells.

In another aspect, the disclosure features a method of treating a EGFR-associated disorder in a subject. The subject may be human, equine, porcine, bovine, murine, canine, feline, and avian subjects. Other warm blooded animals are also included in this invention. The method includes: administering to the subject an anti-EGFR antibody or antibody fragment, in an amount sufficient to treat (e.g., improve or prevent) the EGFR-associated disorder. The anti-EGFR antibody or antibody fragment can be administered to the subject, alone or in combination with other therapeutic modalities as described herein. In one embodiment, the subject is a mammal, e.g., a human, e.g., a human having a EGFR-associated disorder, e.g., a disorder disclosed herein. The antibody can be used to ameliorate one or more symptoms of such disorders. The term "treating" refers to administering a therapy in an amount, manner, and/or mode effective to improve or prevent a condition, symptom, or parameter associated with a disorder (e.g., a disorder described herein) or to prevent onset, progression, or exacerbation of the disorder, to either a statistically significant degree or to a degree detectable to one skilled in the art. Accordingly, treating can achieve therapeutic and/or prophylactic benefits. An effective amount, manner, or mode can vary depending on the subject and may be tailored to the subject. In some embodiments, an anti-EGFR antibody described herein is used for the preparation of a medicament for the treatment of an EGFR-associated disorder.

In some embodiments, the EGFR-associated disorder is cell proliferation associated disorders wherein EGFR is abnormally expressed including, but not limited to, cancers of the bladder, brain, head and neck, pancreas, lung, breast, ovary, colon, prostate, skin and kidney. Examples of cell proliferation disorders include, but are not limited to, hypergammaglobulinemia, lymphoproliferative disorders, paraproteinemias, purpura, sarcoidosis, Sezary Syndrome, Waldenstron's Macroglobulinemia, Gaucher's Disease, histiocytosis and any other cell proliferation disease, beside neoplasia, located in an organ system listed above. In other embodiments, the EGFR-associated disorder includes neoplasms located in the abdomen, brain, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

In another aspect, the disclosure features a method of modulating interaction between EGFR and an EGFR ligand. For example, an anti-EGFR antibody can be used to reduce or inhibit binding, between EGFR and an EGFR ligand, such as EGFR. The method comprises contacting EGFR or a complex that contains EGFR with the antibody. The method can be used on cells in vitro or ex vivo. For example, EGFR receptor-expressing cells can be cultured in vitro in culture medium and the contacting step can be effected by adding an anti-EGFR antibody to the culture medium. Alternatively, the method can be performed on cells present in a subject, e.g., as part of an in vivo (e.g., therapeutic or prophylactic) protocol. For example, the anti-EGFR antibody can be delivered locally or systemically. In one embodiment, an anti-EGFR antibody or antibody fragment described herein is used for the preparation of a medicament for modulating interaction between EGFR and an EGFR ligand.

Generally, the anti-EGFR antibody is provided in an effective amount, e.g., so that contacting the EGFR ligand/EGFR mixture with the anti-EGFR antibody modulates (e.g., interferes with, inhibits, blocks or otherwise reduces) the interaction between EGFR and the EGFR ligand or at least one function of EGFR, e.g., EGFR mediated signaling.

In another aspect, the disclosure provides compositions, e.g., pharmaceutical compositions, that include a pharmaceutically acceptable carrier and an anti-EGFR antibody or antibody fragment disclosed herein.

An anti-EGFR antibody or antibody fragment can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt such as an acid addition salt or a base addition salt. See Berge, S. M., et al. (1977) *J. Pharm. Sci.* 66: 1-19.

Pharmaceutical formulation is a well-established art, and is further described in the literature. See Gennaro (ed.), *Remington: The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients American Pharmaceutical Association*, 3$^{rd}$ ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, the anti-EGFR antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the anti-EGFR antibody or antibody fragment may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See *Sustained and Controlled Release Drug Delivery Systems*, J. R. Robinson, ed., Marcel Dekker, Inc., New York (1978).

In some embodiments, the anti-EGFR antibody or antibody fragment can be modified with a moiety that improves its stabilization and/or retention in circulation, (e.g., in blood, serum, or other tissues) by several fold (e.g., 1.5-, 2-, 5-, 10-, or 50-fold). The modified antibody can be evaluated to assess whether it can reach sites of interests.

For example, the anti-EGFR antibody or antibody fragment can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, the anti-EGFR antibody can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

Compositions can be administered individually to a patient or can be administered in combination with other agents, drugs or hormones. According to some aspects, antibodies can be conjugated with these agents. A summary of the ways in which the antibodies of the present invention can be used therapeutically includes direct cytotoxicity by the antibody, either mediated by complement or by effector cells, or conjugated to anti-tumor drugs, toxins, and radionuclides. Antibodies can also be used for ex vivo removal of tumor cells from the circulation or from bone marrow.

In some embodiments, the anti-EGFR antibody or antibody fragment can also be coupled to or otherwise associated with a label or other agent, such as another therapeutic agent such as a cytotoxic or cytostatic agent. Examples of cytotoxic and chemotherapeutic agents include taxol, cytochalasin B, gramicidin D, vinblastine, doxorubicin, daunorubicin, a maytansinoid (e.g., maytansinol or the DM1 maytansinoid, a sulfhydryl-containing derivative of maytansine), mitoxantrone, mithramycin, actinomycin D, 1-dehydrotestosterone, glucocorticoids, procaine, taxane, tetracaine, lidocaine, propranolol, and puromycin and analogs or homologs thereof. Cytotoxic proteins can include, but are not limited to, Ricin-A, *Pseudomonas* toxin, Diphtheria toxin, and tumor necrosis factor. Diagnostic radionuclides and cytotoxic agents such as cytotoxic radionuclides, drug and proteins can also be conjugated to the antibodies of the present invention. Examples of radionuclides which can be coupled to antibodies and selectively delivered in vivo to sites of antigen include $^{212}$Bi, $^{131}$I, $^{186}$Re, and $^{90}$Y, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

When the anti-EGFR antibody or antibody fragment is used in combination with a second agent (e.g., an anti- TNF-α antibody or other agent), the two agents can be formulated separately or together. The agents can be formulated or otherwise used in a synergistically effective amount. It is also possible to use one or both of the agents in amounts less than would be used for mono-therapy. For example, the respective pharmaceutical compositions can be mixed, e.g., just prior to administration, and administered together or can be administered separately, e.g., at the same or different times.

The anti-EGFR antibody or antibody fragment can be administered to a subject, e.g., a human subject, by a variety of methods. For many applications, the route of administration is one of: intravenous injection or infusion (IV), subcutaneous injection (SC), intraperitoneally (IP), or intramuscular injection. It is also possible to use intra-articular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration may be directly to a site of interest, e.g., a solid tumor.

The route and/or mode of administration of the antibody can also be tailored for the individual case, e.g., by monitoring the subject, e.g., using tomographic imaging, neurological exam, and standard parameters associated with the particular disorder, e.g., criteria for assessing cancer.

The antibody can be administered as a fixed dose, or in a mg/kg dose. The dose can also be chosen to reduce or avoid production of antibodies against the anti-EGFR antibody. Dosage regimens are adjusted to provide the desired response, e.g., a therapeutic response or a combinatorial therapeutic effect. An effective amount for a subject can depend upon the severity of the disease state, the general health of the subject, the age, weight and gender of the subject, diet, time and frequency of administration, drug combination(s), reaction sensitivities and tolerance/response to therapy and can be determined by routine experimentation and is within the judgment of the clinician. Generally, an effective dose will be from 0.01 mg/kg to 50 mg/kg, 0.1 mg/kg to 20 mg/kg, about 1 mg/kg to about 15 mg/kg. Generally, doses of the anti-EGFR antibody (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used.

A dose at which the antibody molecule of the present invention is administered depends on the nature of the condition to be treated, and on whether the antibody molecule is being used prophylactically or to treat an existing condition. If administered prophylactically (i.e., as a vaccine), the antibody is administered in an amount effective to elicit an immune response in the subject. Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the antibody may be administered via continuous infusion. If the antibody molecule has a short half-life (e.g. 2 to 10 hours), it can be necessary to give one or more doses per day. Alternatively, if the antibody molecule has a long half-life (e.g. 2 to 15 days) it can only be necessary to give a dosage once per day, per week or even once every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

In some embodiments, an anti-EGFR antibody or antibody fragment dose can be administered, e.g., at a periodic interval over a period of time (a course of treatment) sufficient to encompass at least 2 doses, 3 doses, 5 doses, 10 doses, or more (e.g., once or twice daily, about one to four times per week, weekly, biweekly, monthly, between about 1 to 12 weeks, between 2 to 8 weeks, between about 3 to 7 weeks, and for about 4, 5, or 6 weeks). Factors that may influence the dosage and timing required to effectively treat a subject, include, but are not limited to, the severity of the disease or disorder, formulation, route of delivery, previous treatments, the general health and/or age of the subject, and other diseases present. Moreover, treatment of a subject with a therapeutically effective amount of a compound can include a single treatment or, can include a series of treatments. Animal models can also be used to determine a useful dose, e.g., an initial dose or a regimen.

If a subject is at risk for developing a disorder described herein, the antibody can be administered before the full onset of the disorder, e.g., as a preventative measure. The duration of such preventative treatment can be a single dosage of the antibody or the treatment may continue (e.g., multiple dosages). For example, a subject at risk for the disorder or who has a predisposition for the disorder may be treated with the antibody for days, weeks, months, or even years so as to prevent the disorder from occurring or fulminating.

A pharmaceutical composition may include a "therapeutically effective amount" of an agent described herein. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model can also be used to determine the appropriate concentration range and route of administration. Such information can then be used to determine useful doses and routes for administration in humans.

Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

In some embodiments, the present invention relates to the use of the anti-EGFR antibody or antibody fragment disclosed herein as a medicament, in particular for use in the treatment or prophylaxis of cancer or for use in a precancerous condition or lesion. The cancer may be, for example, lung cancer, non-small cell lung (NSCL) cancer, bronchioalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

In one aspect, the present invention relates to a method for treating an EGFR-related disorder comprising predicting a response to anti-EGFR therapy in a subject in need of treatment by assaying a sample from the subject prior to therapy with one or a plurality of reagents that detect expression and/or activation of predictive biomarkers for an EGFR-related disorder such as cancer; determining a pattern of expression and/or activation of one or more of the predictive biomarkers, wherein the pattern predicts the subject's response to the anti-EGFR therapy; and administering to a subject who is predicted to respond positively to anti-EGFR treatment a therapeutically effective amount of a composition comprising an anti-EGFR antibody or antibody fragment of the present invention.

As used herein, a subject who is predicted to respond positively to anti-EGFR treatment is one for whom anti-EGFR treatment will have a measurable effect on the EGFR-related disorder (e.g., tumor regression/shrinkage) and for whom the benefits of anti-EGFR therapy are not outweighed by adverse effects (e.g., toxicity).

As used herein, a sample means any biological sample from an organism, particularly a human, comprising one or more cells, including single cells of any origin, tissue or biopsy samples which has been removed from organs such as breast, lung, gastrointestinal tract, skin, cervix, ovary, colon, prostate, kidney, brain, head and neck, or any other organ or tissue of the body, and other body samples including, but not limited to, smears, sputum, secretions, cerebrospinal fluid, bile, blood, lymph fluid, urine and feces.

In some aspects, the present invention relates to a method of treating or preventing the progression of an EGFR-related disorder in a subject, wherein the method comprises administering to the subject an effective amount of the antibody or antibody fragment disclosed herein.

In other aspects, the present invention relates to a method of ameliorating at least one symptom associated with an EGFR-related disorder in a subject, wherein the method comprises administering to the subject an effective amount of the antibody or antibody fragment disclosed herein.

In further aspects, a method of monitoring a subject for the presence, progression, regression or stabilization of an EGFR-related disorder, or for determining the stage of an EGFR-related disorder in a subject is encompassed, the method comprising contacting the subject, or a cell, tissue, organ, fluid, or any other sample of the subject, with an effective amount of at least one antibody described herein, and determining the presence and optionally the quantity of a complex comprising an EGFR ligand and the antibody, wherein the presence of the complex is diagnostic of an EGFR-related disorder; and optionally comparing the quantity of any complex to the quantity of that complex that was detected in a similar assay done at an earlier time on the same subject or to a control, wherein a change in the quantity indicates the presence, progression, regression or stabilization of an EGFR-related disorder.

Pharmaceutical compositions that include the anti-EGFR antibody or antibody fragment can be administered with a medical device. The device can designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include anti-EGFR antibody, and can be configured to deliver one or more unit doses of the antibody. The device can be further configured to administer a second agent, e.g., an anti-TNF-α antibody, either as a single pharmaceutical composition that also includes the anti-EGFR antibody or as two separate pharmaceutical compositions.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

An anti-EGFR antibody can be provided in a kit. In one embodiment, the kit includes (a) a container that contains a composition that includes the anti-EGFR antibody, and optionally (b) informational material. The informational material can be descriptive, instructional, marketing or other material that relates to the methods described herein and/or the use of the agents for therapeutic benefit.

In an embodiment, the kit also includes a second agent. For example, the kit includes a first container that contains a composition that includes the anti-EGFR antibody, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-EGFR antibody (e.g., in a suitable dose, dosage form, or mode of administration such as a dose, dosage form, or mode of administration described herein), to treat a subject who has or who is at risk for a disorder described herein. The information can be provided in a variety of formats, include printed text, computer readable material, video recording, or audio recording, or information that provides a link or address to substantive material, e.g., on the internet.

In addition to the antibody, the composition in the kit can include other ingredients, such as a solvent or buffer, a stabilizer, or a preservative. The antibody can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, (e.g., sterile water or buffer) can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-EGFR antibody and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

Example 1. Production of Anti-EGFR Monoclonal Antibodies

The mouse anti-human EGFR monoclonal antibody (AB-EGFR mAb) is produced by immunizing mice with a native EGFR antigen. The monoclonal antibody detects a 71.1 kDa recombinant EGFR.

Recombinant human EGFR is purchased from Abnova, Inc. The protein from Abnova corresponds to the N-terminus of EGFR (i.e., the extracellular portion of EGFR), and consists of amino acid residues 1 through 405 of EGFR. The EGFR protein is loaded on 8% tris-glycine SDS-PAGE gel. Western blot detection is performed after protein is transferred to PVDF membrane using AB-EGFR mAb. The analysis shows that AB-EGFR mAb is capable of binding to recombinant EGFR (see FIG. 4).

Example 2. Detection of EGFR in A431 and SKBR3 Cells

EGFR-expressing A-431 human vulva cancer cells (FIG. 5A) and SKBR3 human breast cancer cells (FIG. 5B) were seeded in glass-bottom 96-well cell culture plates and incubated overnight. The cells were fixed with 10% formaldehyde. Indirect immunofluorescent staining was performed using 1 µg/mL AB-EGFR mAb in 10% normal donkey serum containing PBS buffer (primary antibody), and a FITC-labeled goat anti-mouse secondary antibody in 10% normal donkey serum containing PBS buffer was applied. Images were visualized by a fluorescence microscope at 63× magnification. The image illustrates the capability of AB-EGFR mAb to bind native EGFR expressed on the cell membranes of A-431 and SKBR3 cells.

Example 3: Comparison of AB-EGFR mAb with Commercial Anti-EGFR Antibodies

EGFR-expressing A-431 human vulva cancer cells were seeded in glass-bottom 96-well cell culture plates and incubated overnight. The cells were fixed with 10% formaldehyde. Indirect immunofluorescent staining was performed using 1 µg/mL Millipore monoclonal anti-EGFR antibody (05-101), Abcam monoclonal anti-EGFR antibody (ab93051), and AB-EGFR mAb, all in 10% normal donkey serum containing PBS buffer. FITC-labeled goat anti-mouse secondary antibody or FITC-labeled donkey anti-rabbit antibody in 10% normal donkey serum containing PBS buffer was applied. DAPI stain was used to stain the nuclei. Images were visualized by a fluorescence microscope. The images show weak membrane staining by Abcam ab93051 antibody (See FIG. 6B); and strong membrane staining (localization of EGFR) by Millipore 05-101 antibody (See FIG. 6A) and AB-EGFR mAb (See FIG. 6C).

Example 4: Detection of Phosphorylated Soluble EGFR by AB-EGFR mAb

Culture medium from confluent EGFR-expressing A-431 human vulva cancer cells was collected, centrifuged, and immunoprecipitated with monoclonal anti-phosphotyrosine antibodies (See lanes 1, 3, and 5 in FIG. 7) or anti-EGFR antibodies: Millipore monoclonal anti-EGFR antibody (05-101), Abcam monoclonal anti-EGFR antibody (ab93051), or AB-EGFR mAb (See lanes 2, 4, and 6, respectively in FIG. 7). IP's were incubated overnight at 4° C. Protein G was added and incubated further at 4° C. Post-incubation, Protein G was washed with RIPA buffer and sample buffer was added. The samples were loaded onto a 8% tris-glycine SDS-PAGE gel. Western blot detection was performed after protein was transferred to PVDF membrane. The primary antibodies used in the assay were anti-EGFR antibodies: Millipore 05-101 (See lanes 1 and 2 in FIG. 7), Abcam ab93051 (See lanes 3 and 4 in FIG. 7), and AB-EGFR mAb (See lanes 5 and 6 in FIG. 7). The results show that AB-EGFR recognizes soluble EGFR including soluble phosphorylated EGFR (compare the upper bands in lanes 5 and 6). The results also show that the Millipore 05-101 antibody does not recognize EGFR in this assay (no upper band in lanes 1 or 2). The results also show that the Abcam ab93051 antibody recognizes soluble EGFR in its non-phosphorylated form but not in its phosphorylated form (compare lanes 3 and 4). The lower bands are residual primary antibody fragments that co-precipitated with EGFR.

Example 5. Detection of EGFR in Cancerous Tissues

Slides of formalin fixed, paraffin-embedded samples from patients with lung cancer (FIG. 8A) and colon cancer (FIG. 8B) were contacted with AB-EGFR to determine whether they express EGFR. The slides were deparaffinized and rehydrated by incubating in xylene for 15 minutes twice, in xylene-ethanol for 5 minutes, in 100% ethanol for 5 minutes, in 95%, 75%, and 50% ethanol for 3 minutes each. The slides were rinsed with reagent-quality water for 5 minutes and incubated in proteinase K solution for 10 minutes. After incubation in wash buffer for 5 minutes, twice, the slides were blocked and incubated with AB-EGFR mAb for 1-hour. The slides were washed thrice with wash buffer for 5 minutes and incubated in Mach3 mouse probe (Biocare Medical) for 15 minutes. After a wash, the slides were stained with DAB substrate solution until the desired stain intensity was developed. The slides were washed in 70%, 80%, 95% and 100% ethanol for 2 minutes each, consecutively, and washed in xylene for 2 minutes twice. The slides were dried and mounted. The results show that AB-EGFR mAb detects EGFR in these samples. Thus, AB-EGFR can be used in diagnostic applications to detect EGFR and diagnose at least lung and colon cancer.

Example 6. Comparison of AB-EGFR mAb with Dako-EGFR mAb

Slides of formalin fixed, paraffin-embedded breast cancer tissue samples were stained using AB-EGFR mAb (See top row in FIGS. 9A-H) and DAKO-EGFR mAb (See bottom row in FIG. 9). DAKO-EGFR is obtained from the FDA-approved EGFR detection kit, Dako pharmDx™. The staining protocol for AB-EGFR mAb is described in Example 5. The staining protocol for DAKO-EGFR mAb is according to the instructions in the kit. FIGS. 9A-H shows that the AB-EGFR and Dako-EGFR mAbs are capable of detecting EGFR expression in breast cancer tissues.

Other embodiments of the present invention will be apparent to those skilled in the art from consideration of the specification and practice of the present invention disclosed herein. It is intended that the specification and examples be considered as exemplary only, with a true scope and spirit of the present invention being indicated by the following claims.

Example 7. Sensitivity and Specificity

Three tissue microarrays containing 96 breast carcinoma tissues and 70 controls from cancer adjacent normal breast tissues were included for evaluation of the sensitivity and specificity of Alper-EGFR antibody and the comparison with a FDA approved commercial EGFR pharmDx™ Kit. The microarrays were purchased from US Biomax, Inc (Rockville, Md.) and BioChain Institute, Inc (Newark, Calif.), and EGFR pharmDx™ Kit was obtained from DAKO (Carpinteria, Calif.). The two sets of microarrays were separately stained using either Alper-EGFR antibody or EGFR pharmDx™ Kit. The staining using EGFR pharmDx™ Kit was performed following the kit instruction, while the staining using Alper-EGFR antibody was conducted following the procedure described herein. The tissue sections were deparaffinized and rehydrated. The antigen retrieval was performed by incubation of tissue sections with proteinase K for 10 minutes. After blocking with 3% peroxidase blocking buffer and Blocking Sniper (Biocare Medical, Concord, Calif.), the sections was incubated in Alper-EGFR antibody solution (1:120 in Antibody Diluent, DAKO) for 1 hour at room temperature (RT). The sections were incubated for 15 minutes at RT with MACH 3 Probe and then following 15 minutes of incubation with MACH 3 Mouse Polymer. The visualization was completed by applying DAB substrate solution to the sections and incubated until optimal color develops.

The specific membrane staining of EGFR was evaluated and scored by independent pathologist in Cytology Services of Maryland (Laurel, Md.). The specificity and sensitivity for Alper-EGFR antibody and DAKO EGFR pharmDx™ Kit was calculated based on the scores from respective staining.

EGFR protein is over expressed and amplified in breast cancers. Alper EGFR and DAKO-EGFR antibodies bind to different epitopes on EGFR protein. Alper EGFR binds to N terminal of EGFR, and DAKO-EGFR binds to transmembrane domain of EGFR. Tables 1-4 display frequency distribution and corresponding Sensitivity and Specificity.

TABLE 1

| Alper EGFR | Disease: Breast Cancer | No Disease: No Breast Cancer | Total |
|---|---|---|---|
| Positive | 19 | 0 | 14 |
| Negative | 77 | 70 | 142 |
| Total | 96 | 70 | 156 |

Sensitivity of Alper EGFR in breast carcinoma (ESTIMATED using the data in Table 1): 19/96=0.16 (20%).

Specificity of Alper EGFR (ESTIMATED using the data in table 1): 70/70=1.00 (100%).

TABLE 2

| DAKO EGFR | Disease: Breast Cancer | No Disease: No Breast Cancer | Total |
|---|---|---|---|
| Positive | 5 | 0 | 5 |
| Negative | 91 | 70 | 151 |
| Total | 96 | 70 | 156 |

Sensitivity of DAKO EGFR (ESTIMATED using the data in table 2): 5/96=0.052 (5%).

Specificity of DAKO EGFR (ESTIMATED using the data in table 2): 70/70=1.00 (100%).

TABLE 3

Comparison of AB-EGFR and commercial EGFR antibodies.

| | Alper-EGFR antibody | Commercial EGFR antibody |
|---|---|---|
| Sensitivity (%) | 20 | 5 |
| Specificity (%) | 100 | 100 |

From the data above, Alper-EGFR antibody is more sensitive than the commercially available DAKO EGFR antibody.

What is claimed is:

1. An isolated antibody specific for epithelial growth factor receptor (EGFR), comprising:
a light chain variable domain comprising at least one complementarity determining region (CDR) selected from SEQ ID NOs:3, SEQ ID NO:4, and SEQ ID NO:5, and
a heavy chain variable domain comprising at least one CDR selected from SEQ ID NOs:6, SEQ ID NO:7, and SEQ ID NO:8.

2. The antibody of claim 1, wherein the light chain comprises:
SEQ ID NO:1, and
the heavy chain comprises SEQ ID NO:2.

3. The antibody of claim 1, wherein the antibody is capable of preferentially binding to the extracellular domain of EGFR.

4. An isolated antibody specific for EGFR, comprising:
- a light chain variable domain comprising three CDRs comprising SEQ ID NO:3, SEQ ID NO:4, and SEQ ID NO:5, and
- a heavy chain variable domain comprising three CDRs comprising SEQ ID NO:6, SEQ ID NO:7, and SEQ ID NO:8.

5. An isolated antibody specific for EGFR, comprising a light chain variable domain comprising:
- a) a CDR1 comprising SEQ ID NO:3,
- b) a CDR2 comprising SEQ ID NO:4, and
- c) a CDR3 comprising SEQ ID NO:5; and a heavy chain variable domain comprising:
- a) a CDR1 comprising SEQ ID NO:6,
- b) a CDR2 comprising SEQ ID NO:7, and
- c) a CDR3 comprising SEQ ID NO:8.

6. The antibody of claim 1, wherein the antibody is capable of binding to EGFR with an affinity of between $10^{-8}$ and $10^{-11}$ M.

7. The antibody of claim 1, wherein the antibody is humanized.

8. The antibody of claim 1, wherein the antibody is capable of selectively reducing the activity of EGFR.

9. The antibody of claim 1, wherein the antibody is labeled.

10. The antibody of claim 1, wherein the antibody is labeled fluorescently, with an enzyme, or with a radioisotope.

11. A kit comprising:
- (a) the antibody of claim 1; and
- (b) a secondary antibody conjugated to a detectable label, or the antibody of claim 1 that has been further modified to be detectably labeled.

12. A Pharmaceutical composition comprising the antibody of claim 1 and a pharmaceutically acceptable carrier and/or diluent.

* * * * *

SEQUENCE LISTING

<160> NUMBER OF SEQ ID NOS: 20

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Thr Gln Ser Pro Ser Ser Leu Ser Ala Ser Leu Gly Glu Arg Val
1               5                   10                  15

Ser Leu Thr Cys Gln Ala Ser Gln Gly Ile Ser Asn Asn Leu Asn Trp
            20                  25                  30

Tyr Gln Gln Thr Pro Gly Lys Ala Pro Arg Leu Leu Ile Tyr Asp Ala
        35                  40                  45

Ser Lys Leu Glu Asp Gly Val Pro Ser Arg Phe Ser Gly Thr Gly Tyr
50                  55                  60

Arg Thr Asp Phe Asn Phe Thr Ile Ser Ser Leu Glu Glu Glu Asp Val
65                  70                  75                  80

Ala Thr Tyr Phe Cys Leu Gln His Arg Tyr Leu Pro Val His Val Arg
                85                  90                  95

Arg Gly Asp Gln Val Gly Asn Lys Thr Gly
            100                 105

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Val Thr Leu Lys Val Cys Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Leu Arg Gln Pro Ser Gly Lys Ser Leu Glu
        35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Thr Asp Thr Ala Thr Tyr Tyr
                85                  90                  95

Cys Ala Arg Met Gly Met Thr Gly Tyr Phe Asp Phe Trp Gly Gln Gly
            100                 105                 110

Thr Thr Leu Thr Val Ser Ser
        115

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gln Gly Ile Ser Asn Asn
1               5

<210> SEQ ID NO 4
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ala Ser
1

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Gln His Arg Tyr Leu Pro Val His
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Ser Leu Ser Thr Ser Gly Met Gly
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Trp Trp Asp Asp Asp Lys
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Met Gly Met Thr Gly Tyr Phe Asp Phe
1               5                   10

<210> SEQ ID NO 9
<211> LENGTH: 321
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 9

| atgacccagt ctccatcctc cctgtctgca tctttgggag agagagtctc cctgacttgc | 60 |
| caggcaagtc agggcattag caataattta aactggtatc aacaaacacc agggaaagct | 120 |
| cctaggctct tgatctatga tgcaagcaaa ttggaagatg gggtcccttc aaggttcagt | 180 |
| ggcactggat atcggacaga tttcaatttc accatcagca gcctggagga agaagatgtg | 240 |
| gcaacttatt tctgtctaca gcataggtat ctccccgtac acgttcggag ggggaccaa | 300 |
| gttggaaata aaacgggctg a | 321 |

<210> SEQ ID NO 10
<211> LENGTH: 287
<212> TYPE: DNA
<213> ORGANISM: Mus musculus

<400> SEQUENCE: 10

| gatgtccaga tgattcagtc tccatcctcc ctgtctgcat ctttgggaga catagtcacc | 60 |
| atgacttgcc aggcaagtca gggcactagc attaatttaa actggtttca gcaaaaacca | 120 |
| gggaaagctc ctaagctcct gatctatggt gcaagcaact tggaagatgg ggtcccatca | 180 |
| aggttcagtg gcagtagata tgggacagat ttcactctca ccatcagcag cctggaggat | 240 |
| gaagatatgg caacttattt ctgtctacag catagttatc tccctcc | 287 |

<210> SEQ ID NO 11
<211> LENGTH: 287
<212> TYPE: DNA
<213> ORGANISM: Mus musculus

<400> SEQUENCE: 11

| gacatcaaga tgacccagtc tccatcttcc atgtatgcat ctctaggaga gagagtcact | 60 |
| atcacttgca aggcgagtca ggacattaat agctatttaa gctggttcca gcagaaacca | 120 |
| gggaaatctc ctaagaccct gatctatcgt gcaaacagat ggtagatgg ggtcccatca | 180 |
| aggttcagtg gcagtggatc tgggcaagat tattctctca ccatcagcag cctggagtat | 240 |
| gaagatatgg gaatttatta ttgtctacag tatgatgagt ttcctcc | 287 |

<210> SEQ ID NO 12
<211> LENGTH: 287
<212> TYPE: DNA
<213> ORGANISM: Mus musculus

<400> SEQUENCE: 12

| gacatcaaga tgacccagtc tccatcctcc atgtatgcat cgctgggaga gagagtcact | 60 |
| atcacttgca aggcgagtca ggacattaaa agctatttaa gctggtacca gcagaaacca | 120 |
| tggaaatctc ctaagaccct gatctattat gcaacaagct ggcagatgg ggtcccatca | 180 |
| agattcagtg gcagtggatc tgggcaagat tattctctaa ccatcagcag cctggagtct | 240 |
| gacgatacag caacttatta ctgtctacag catggtgaga gccctcc | 287 |

<210> SEQ ID NO 13
<211> LENGTH: 287
<212> TYPE: DNA
<213> ORGANISM: Mus musculus

<400> SEQUENCE: 13

```
gacatcctga tgacccaatc tccatcctcc atgtctgtat ctctgggaga cacagtcagc    60
atcacttgcc atgcaagtca gggcattagc agtaatatag gtggttgca gcagaaacca    120 gggaaatcat ttaagggcct gatctatcat ggaaccaact tggaagatgg agttccatca   180
aggttcagtg gcagtggatc tggagcagat tattctctca ccatcagcag cctggaatct   240
gaagattttg cagactatta ctgtgtacag tatgctcagt ttcctcc                 287
```

<210> SEQ ID NO 14
<211> LENGTH: 287
<212> TYPE: DNA
<213> ORGANISM: Mus musculus

<400> SEQUENCE: 14

```
gaaatccaga tgacccagtc tccatcctct atgtctgcat ctctgggaga cagaataacc   60
atcacttgcc aggcaactca agacattgtt aagaatttaa actggtatca gcagaaacca   120
gggaaacccc cttcattcct gatctattat gcaactgaac tggcagaagg ggtcccatca   180
aggttcagtg gcagtgggtc tgggtcagac tattctctga caatcagcaa cctggagtct   240
gaagattttg cagactatta ctgtctacag ttttatgagt ttcctcc                 287
```

<210> SEQ ID NO 15
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
ttggttactc tgaaagtgtg tggccctggg atattgcagc cctcccagac cctcagtctg   60
acttgttctt tctctggggtt ttcactgagc acttctggta tgggtgtagg ctggcttcgt  120
cagccttcag ggaagagtct ggagtggctg gcacacattt ggtgggatga tgataagcgc   180
tataacccag ccctgaagag ccgactgaca atctccaagg atacctccag caaccaggta   240
ttcctcaaga tcgccagtgt ggacactaca gatactgcca catactactg tgctcgaatg   300
ggcatgaccg gctactttga cttctggggc caaggcacca ctctcacagt ctcctcag    358
```

<210> SEQ ID NO 16
<211> LENGTH: 300
<212> TYPE: DNA
<213> ORGANISM: Mus musculus

<400> SEQUENCE: 16

```
caggttactc tgaaagagtc tggccctggg atattgcagc cctcccagac cctcagtctg   60
acttgttctt tctctggggtt ttcactgagc acttttggta tgggtgtagg ctggattcgt  120
cagccttcag ggaagggtct ggagtggctg gcacacattt ggtgggatga tgataagtac   180
tataacccag ccctgaagag tcggctcaca atctccaagg atacctccaa aaaccaggta   240
ttcctcaaga tcgccaatgt ggacactgca gatactgcca catactactg tgctcgaata   300
```

<210> SEQ ID NO 17
<211> LENGTH: 301
<212> TYPE: DNA
<213> ORGANISM: Mus musculus

<400> SEQUENCE: 17

```
cagattactc agaaagagtc tggccctggg atattgcagc cctcccagac cctcagtctg   60
```

```
acttgttctt tctctgggtt ttcactgagc acttctggta tgggtgtagg ctggattcat    120
cagccttcag ggaatggtct ggagtggctg gcacacattt ggtggaatga taataagtac    180
tataacacag ccctgaagag ccggctcaca atctccaagg atacctccaa caaccaggta    240
ttcctcaaga tcgccagtgt ggacactgca gatactgcca catactactg tgctcgaata    300
g                                                                    301

<210> SEQ ID NO 18
<211> LENGTH: 301
<212> TYPE: DNA
<213> ORGANISM: Mus musculus

<400> SEQUENCE: 18
caggttactc tgaaagagtc tggccctggg atattgcagt cctcccagac cctcagtctg     60
acttgttctt tctctgggtt ttcactgagc acttctggta tgggtgtgag ctggattcgt    120
cagccttcag gaaagggtct ggagtggctg gcacacattt actgggatga tgacaagcgc    180
tataacccat ccctgaagag ccggctcaca atctccaagg atacctccag aaaccaggta    240
ttcctcaaga tcaccagtgt ggacactgca gatactgcca catactactg tgctcgaaga    300
g                                                                    301

<210> SEQ ID NO 19
<211> LENGTH: 301
<212> TYPE: DNA
<213> ORGANISM: Mus musculus

<400> SEQUENCE: 19
caggttactc tgaaagagtc tggccctggg atattgcagc cctcccagac cctcagtctg     60
acttgttctt tctctgggtt ttcactgagc acttctaata tgggtatagg ctggattcgt    120
cagccttcag ggaagggtct agagtggctg gcacacattt ggtggaatga tgataagtac    180
tataacccat ccctgaagag ccggctcaca atctccaagg atacctccaa caaccaggta    240
ttcctcaaga tcaccagtgt ggacactgca gatactgcca catactactg tgctcaaata    300
g                                                                    301

<210> SEQ ID NO 20
<211> LENGTH: 285
<212> TYPE: DNA
<213> ORGANISM: Mus musculus

<400> SEQUENCE: 20
caggttactc tgaaagagtc tggccctggt atattgcagc cctcccagac cctcagtctg     60
acttgttctt tctctgggtt ttcactgagc acttttggta tgggtatagg ctggattcgt    120
cagccttcag ggaagggtct agagtggctg gcacacattt ggtgggatga tgataagtac    180
tataacccag ccctgaagag tcggctcaca atctccaagg atacctccaa caaccaggta    240
ttcctcaaga tcaccagtgt ggacactgca gatactgcca catac                    285
```